US011414401B2

(12) United States Patent
Peng et al.

(10) Patent No.: US 11,414,401 B2
(45) Date of Patent: Aug. 16, 2022

(54) SUBSTITUTED 2-ANILINOPYRIMIDINE DERIVATIVES AS EGFR MODULATORS

(71) Applicants: Beta Pharma, Inc., Wilmington, DE (US); Beta Pharma (Shanghai) Co., Ltd., Shanghai (CN)

(72) Inventors: Jirong Peng, Mequon, WI (US); Michael John Costanzo, Warminster, PA (US); Michael Nicholas Greco, Lansdale, PA (US); Michael Alan Green, Easton, PA (US); Victoria Lynn Wilde, Montclair, NJ (US); Don Zhang, Princeton, NJ (US)

(73) Assignees: BETA PHARMA INC., Princeton, NJ (US); BETA PHARMA (SHANGHAI) CO., LTD., Shanghai (CN)

( * ) Notice: Subject to any disclaimer, the term of this patent is extended or adjusted under 35 U.S.C. 154(b) by 18 days.

(21) Appl. No.: 16/819,539

(22) Filed: Mar. 16, 2020

(65) Prior Publication Data
US 2020/0216421 A1 Jul. 9, 2020

Related U.S. Application Data

(63) Continuation of application No. 15/534,838, filed as application No. PCT/US2015/065286 on Dec. 11, 2015, now Pat. No. 10,590,111.

(60) Provisional application No. 62/166,883, filed on May 27, 2015, provisional application No. 62/090,869, filed on Dec. 11, 2014.

(51) Int. Cl.
| | |
|---|---|
| C07D 403/04 | (2006.01) |
| C07D 401/14 | (2006.01) |
| C07D 471/04 | (2006.01) |
| C07D 403/14 | (2006.01) |
| A61K 31/506 | (2006.01) |
| A61K 45/06 | (2006.01) |
| A61P 35/00 | (2006.01) |
| A61P 43/00 | (2006.01) |

(52) U.S. Cl.
CPC .......... *C07D 403/04* (2013.01); *A61K 31/506* (2013.01); *A61K 45/06* (2013.01); *C07D 401/14* (2013.01); *C07D 403/14* (2013.01); *C07D 471/04* (2013.01)

(58) Field of Classification Search
CPC .. C07D 403/04; C07D 401/14; C07D 403/14; C07D 471/04; A61K 45/06; A61K 31/506; A61P 43/00; A61P 35/00
See application file for complete search history.

(56) References Cited

U.S. PATENT DOCUMENTS

| | | | |
|---|---|---|---|
| 7,943,616 B2 | 5/2011 | Cox et al. | |
| 2008/0146565 A1 | 6/2008 | Dunn et al. | |
| 2012/0316135 A1 | 12/2012 | Dalgarno et al. | |
| 2013/0053409 A1 | 2/2013 | Butterworth et al. | |
| 2017/0355696 A1 † | 12/2017 | Jiang | |
| 2019/0152969 A1 | 5/2019 | Jiang | |

FOREIGN PATENT DOCUMENTS

| | | |
|---|---|---|
| CN | 105085489 A | 11/2015 |
| CN | 105461695 A | 4/2016 |
| EP | 3157916 A1 | 4/2017 |
| EP | 3216786 A1 | 9/2017 |
| JP | 2017533266 A | 11/2017 |
| WO | 2001047922 A2 | 7/2001 |
| WO | 2010059711 A1 | 5/2010 |
| WO | 2010129053 A2 | 11/2010 |
| WO | 2013014448 A1 | 1/2013 |
| WO | 2015127872 A1 | 9/2015 |
| WO | 2015195228 A1 | 12/2015 |
| WO | 2016029839 A1 | 3/2016 |
| WO | 2016070816 A1 | 5/2016 |

OTHER PUBLICATIONS

Almatar, M. "Chemotherapeutic agents: Taxol and vincristine isolated from endophytic fungi." (2015) p. 80-88.*
Walter, A.O., "Abstract C189: CO-1686, an orally available, mutant-selective inhibitor of the epidermal growth factor receptor (EGFR), causes tumor shrinkage in non-small cell lung cancer (NSCLC) with T790M mutations." (2011): C189-C189.; p. 1-2.*
Ward et al., "Structure- and Reactivity-Based Development of Covalent Inhibitors of the Activating and Gatekeeper Mutant Forms of the Epidermal Growth Factor Receptor (EGFR)," Journal of Medicinal Chemistry (2013); 56(17):7025-7048.
Walter et al., "Discovery of a mutant-selective covalent inhibitor of EGFR that overcomes T790M-mediated resistance in NSCLC," Cancer Discov. (2013); 3(12):1404-1415.
Martins et al., "Cisplatin and Radiotherapy With or Without Erlotinib in Locally Advanced Squamous Cell Carcinoma of the Head and Neck: A Randomized Phase II Trial," Journal of Clinical Oncology (2013); 31(11):1415-1421.
Zahorowska et al., "Combined therapies for cancer: a review of EGFR-targeted monotherapy and combination treatment with other drugs," J Cancer Res Clin Oncol (2009); 135:1137-1148.
Information about Related Patents and Patent Applications, see section 6 of the accompanying Information Disclosure Statement Letter, which concerns Related Patents and Patent Applications.
Certified Copy Foreign Priority Application No. CN201410619334.7 with a filing date of Nov. 5, 2014 and a certified English translation.†
Notice of Allowance in U.S. Appl. No. 15/524,228, issued by the USPTO dated Nov. 5, 2018.†

* cited by examiner
† cited by third party

*Primary Examiner* — John M Mauro
(74) *Attorney, Agent, or Firm* — Cantor Colburn LLP

(57) ABSTRACT

This application discloses novel substituted 2-anilinopyrimidine derivatives, and pharmaceutically acceptable salts, solvates, prodrugs, and compositions thereof, which are useful for the treatment or prevention of diseases or medical conditions mediated by epidermal growth factor receptors (EGFRs), including but not limited to a variety of cancers.

7 Claims, 4 Drawing Sheets

SUBSTITUTED 2-ANILINOPYRIMIDINE DERIVATIVES AS EGFR MODULATORS

CROSS REFERENCE TO RELATED APPLICATIONS

This application is a Continuation of U.S. patent application Ser. No. 15/534,838, filed Jun. 9, 2017, which is the U.S. National Phase of International Patent Application No. PCT/US2015/065286, filed Dec. 11, 2015, which claims priority under 35 U.S.C. § 119(e) to U.S. Provisional Application No. 62/090,869, filed on Dec. 11, 2014, and No. 62/166,883, filed on May 27, 2015, all of which are incorporated herein by reference in their entireties.

FIELD OF THE INVENTION

The present invention relates to substituted 2-anilinopyrimidine derivatives and pharmaceutically acceptable salts and compositions thereof useful for the treatment or prevention of diseases or medical conditions mediated through mutated forms of epidermal growth factor receptor (EGFR), such as various cancers.

BACKGROUND OF THE INVENTION

The epidermal growth factor receptor (EGFR, Her1, ErbB1) is a principal member of the ErbB family of four structurally-related cell surface receptors with the other members being Her2 (Neu, ErbB2), Her3 (ErbB3) and Her4 (ErbB4). EGFR exerts its primary cellular functions though its intrinsic catalytic tyrosine protein kinase activity. The receptor is activated by binding with growth factor ligands, such as epidermal growth factor (EGF) and transforming growth factor-alpha (TGF-α), which transform the catalytically inactive EGFR monomer into catalytically active homo- and hetero-dimers. These catalytically active dimers then initiate intracellular tyrosine kinase activity, which leads to the autophosphorylation of specific EGFR tyrosine residues and elicits the downstream activation of signaling proteins. Subsequently, the signaling proteins initiate multiple signal transduction cascades (MAPK, Akt and JNK), which ultimately mediate the essential biological processes of cell growth, proliferation, motility and survival.

EGFR is found at abnormally high levels on the surface of many types of cancer cells and increased levels of EGFR have been associated with advanced disease, cancer spread and poor clinical prognosis. Mutations in EGFR can lead to receptor overexpression, perpetual activation or sustained hyperactivity and result in uncontrolled cell growth, i.e. cancer. Consequently, EGFR mutations have been identified in several types of malignant tumors, including metastatic lung, head and neck, colorectal and pancreatic cancers. In lung cancer, mutations mainly occur in exons 18 to 21, which encode the adenosine triphosphate (ATP)-binding pocket of the kinase domain. The most clinically relevant drug-sensitive EGFR mutations are deletions in exon 19 that eliminate a common amino acid motif (LREA) and point mutations in exon 21, which lead to a substitution of arginine for leucine at position 858 (L858R). Together, these two mutations account for nearly 85% of the EGFR mutations observed in lung cancer. Both mutations have perpetual tyrosine kinase activity and as a result they are oncogenic. Biochemical studies have demonstrated that these mutated EGFRs bind preferentially to tyrosine kinase inhibitor drugs such as erlotinib and gefitinib over adenosine triphosphate (ATP).

Erlotinib and gefitinib are oral EGFR tyrosine kinase inhibitors that are first line monotherapies for non-small cell lung cancer (NSCLC) patients having activating mutations in EGFR. Around 70% of these patients respond initially, but unfortunately they develop resistance with a median time to progression of 10-16 months. In at least 50% of these initially responsive patients, disease progression is associated with the development of a secondary mutation, T790M in exon 20 of EGFR (referred to as the gatekeeper mutation). The additional T790M mutation increases the affinity of the EGFR kinase domain for ATP, thereby reducing the inhibitory activity of ATP-competitive inhibitors like gefitinib and erlotinib.

Recently, irreversible EGFR tyrosine kinase inhibitors have been developed that effectively inhibit the kinase domain of the T790M double mutant and therefore overcome the resistance observed with reversible inhibitors in the clinic. These inhibitors possess reactive electrophilic functional groups that react with the nucleophilic thiol of an active-site cysteine. Highly selective irreversible inhibitors can be achieved by exploiting the inherent non-covalent selectivity of a given scaffold along with the location of a particular cysteine residue within the ATP binding site. The acrylamide moieties of these inhibitors both undergo a Michael reaction with Cys797 in the ATP binding site of $EGFR^{T790M}$ to form a covalent bond. This covalent mechanism is thought to overcome the increase in ATP affinity of the T790M EGRF double mutant and give rise to effective inhibition. However, these inhibitors may cause various undesired toxicities. Therefore, development of new inhibitors for treatment of various EGFR-related cancers is still in high demand.

SUMMARY OF THE INVENTION

The present invention provides novel compounds as EGFR tyrosine kinase inhibitors that are therapeutically useful in the treatment or prevention of a number of EGFR-related diseases or disorders, such as various cancers.

In one aspect, the present invention provides compounds of formula I:

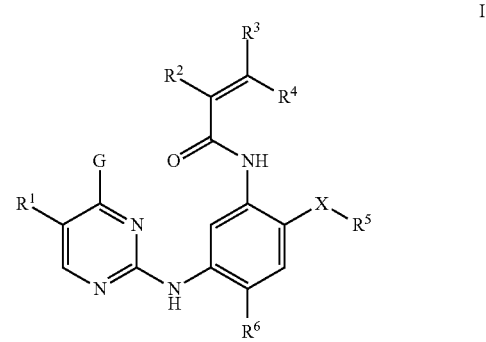

or a pharmaceutically acceptable salt, solvate, or prodrug thereof, wherein:

G is selected from substituted or unsubstituted 1H-indol-3-yl, substituted or unsubstituted 1H-indazol-3-yl, substituted or unsubstituted 2H-indazol-3-yl, and substituted or unsubstituted pyrazolo[1,5-a]-pyridin-3-yl, and substituted or unsubstituted 4,5,6,7-tetrahydropyrazolo[1,5-a]pyridin-3-yl;

X is selected from oxygen, sulfur, and methylene;

$R^1$ is selected from hydrogen, halogen, methyl, trifluoromethyl, and cyano;

$R^2$, $R^3$, and $R^4$ are the same or different and are independently selected from hydrogen, halogen and trifluoromethyl;

$R^5$ is selected from lower alkyl, optionally substituted 3- to 6-membered heterocyclyl, $R^7R^8N$-(lower alkyl), and $R^7R^8N$-(cycloalkylalkyl), wherein $R^7$ and $R^8$ are the same or different and are independently selected from hydrogen and lower alkyl; and $R^6$ is selected from lower alkoxy and lower alkyl.

In some preferred embodiments, in formula I, G is a 1H-indol-3-yl or 1H-indazol-3-yl moiety having a formula

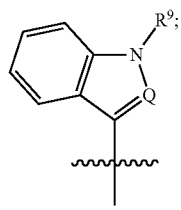

and the present invention provides a compound of formula II:

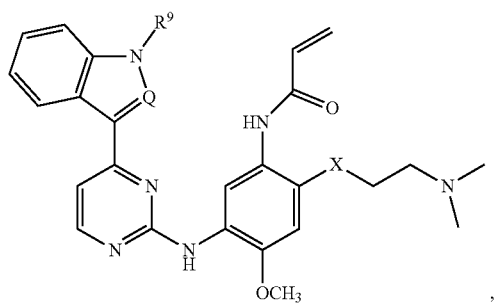

or a pharmaceutically acceptable salt, solvate, or prodrug thereof, wherein:

X is O, S, or $CH_2$;

Q is C—$R^{10}$ or N $R^9$ is $CH_3$ or $CH_2CH_2F$; and $R^{10}$ is H or $CH_3$.

In some other preferred embodiments, in formula I, G is pyrazolo[1,5-a]-pyridin-3-yl, and the present invention provides a compound of formula V:

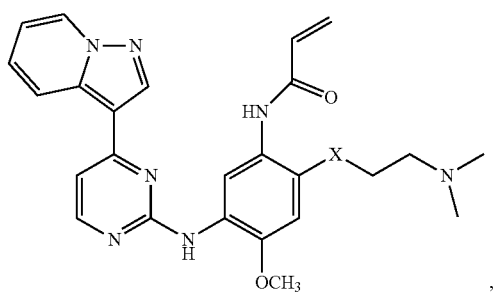

or a pharmaceutically acceptable salt, solvate, or prodrug thereof, wherein X is O, S, or $CH_2$.

In another aspect the present invention provides pharmaceutical compositions comprising any of the compounds, or a pharmaceutically acceptable salt, solvate, or prodrug thereof, and a pharmaceutically acceptable carrier.

The compounds and compositions of the present invention are useful for treating diseases, disorders, or conditions associated with one or more EGFR mutations. Such diseases, disorders, or conditions include those described herein, such as various cancers.

Thus, in another aspect, the present invention provides methods of treating diseases or disorders associated with EGFR activities, such as various cancers associated with one or more EGFR mutations, or use of the compounds or compositions in the manufacture of medicaments for treatment of these diseases or disorders.

In another aspect, the compounds of this invention are useful for the study of kinases in biological and pathological phenomena; the study of transduction pathways mediated by such kinases; and the comparative evaluation of new kinase inhibitors.

In another aspect, the present invention provides methods of synthesizing the compounds disclosed herein.

Other aspects or advantages of the present invention will be better appreciated in view of the detailed description and claims.

DETAILED DESCRIPTION OF THE INVENTION

Figure 1:
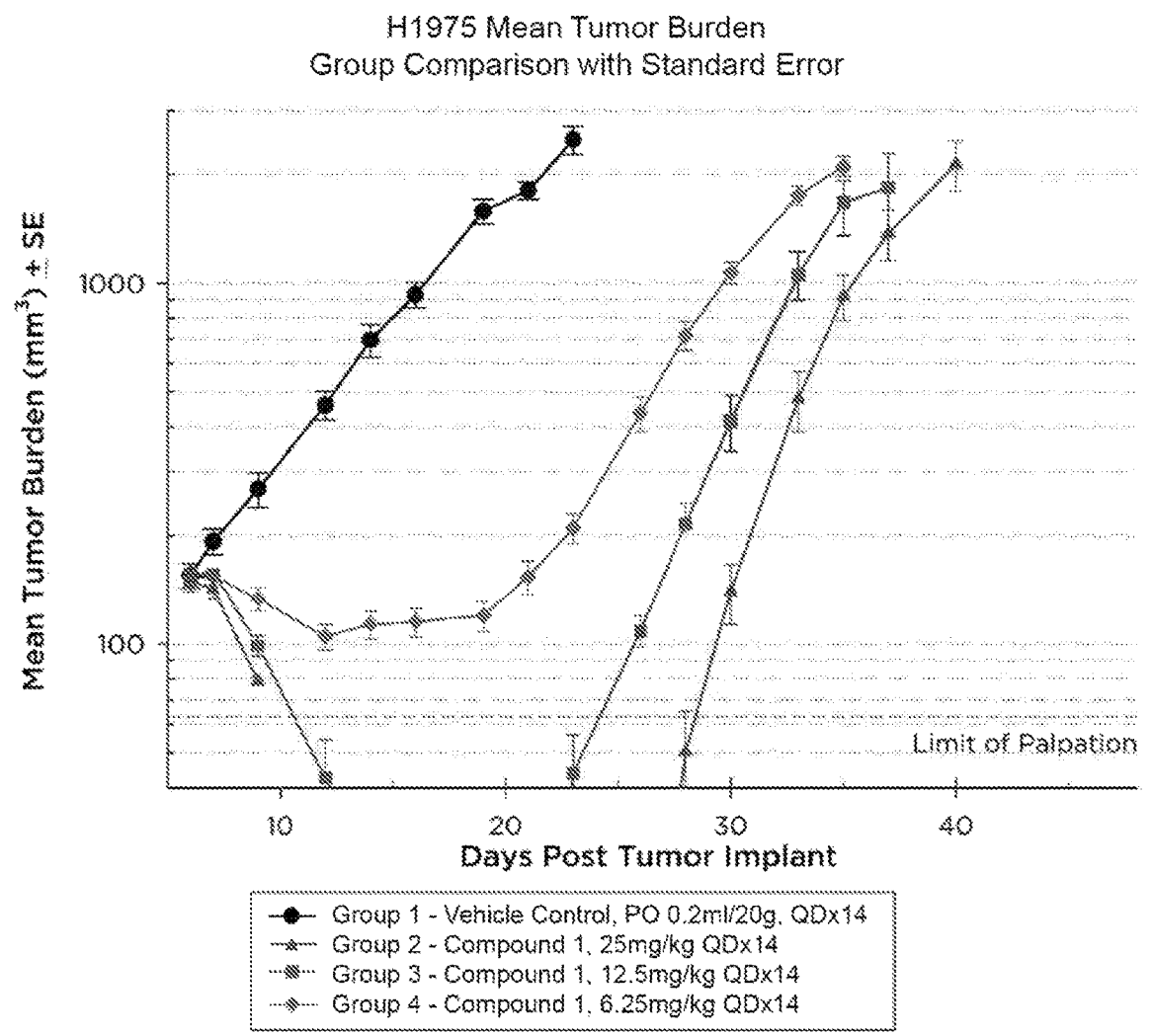
FIG. 1 illustrates the H1975 tumor growth inhibition assay results for Example 1 in mice.

In one aspect, the present invention provides a compound of the formula I:

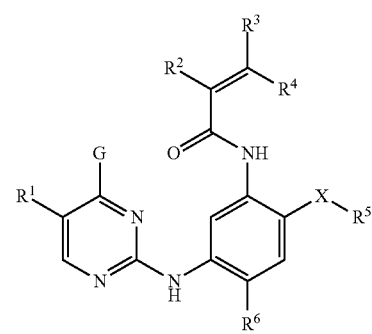

or a pharmaceutically acceptable salt, solvate, or prodrug thereof, wherein:

G is selected from the group consisting of substituted or unsubstituted 1H-indol-3-yl, substituted or unsubstituted 1H-indazol-3-yl, substituted or unsubstituted 2H-indazol-3- yl, substituted or unsubstituted pyrazolo[1,5-a]-pyridin-3-yl, and substituted or unsubstituted 4,5,6,7-tetrahydropyrazolo[1,5-a]pyridin-3-yl;

X is oxygen, sulfur, or methylene;

$R^1$ is hydrogen, halogen, methyl, trifluoromethyl, or cyano;

$R^2$, $R^3$, and $R^4$ are the same or different and are independently selected from the group consisting of hydrogen, halogen, and trifluoromethyl;

$R^5$ is selected from the group consisting of lower alkyl, optionally substituted 3- to 6-membered heterocyclyl, $R^7R^8N$-(lower alkyl), and $R^7R^8N$-(cycloalkylalkyl), wherein $R^7$ and $R^8$ are the same or different and are each independently selected from hydrogen and lower alkyl; and $R^6$ is lower alkoxy or lower alkyl.

In one embodiment of this aspect, G is selected from the group consisting of 1H-indol-3-yl, 1-methyl-1H-indol-3-yl, 1-(2-fluoroethyl)-1H-indol-3-yl, 1,2-dimethyl-1H-indol-3-yl, pyrazolo[1,5-a]-pyridin-3-yl, 4,5,6,7-tetrahydropyrazolo[1,5-a]pyridin-3-yl, 1-methyl-1H-indazol-3-yl, and 2-methyl-2H-indazol-3-yl.

In a preferred embodiment, G is selected from the group consisting of 1-methyl-1H-indol-3-yl, 1-(2-fluoroethyl)-1H-indol-3-yl, 1,2-dimethyl-1H-indol-3-yl, pyrazolo[1,5-a]-pyridin-3-yl, and 1-methyl-1H-indazol-3-yl.

In a more preferred embodiment, G is 1-methyl-1H-indol-3-yl, 1-(2-fluoroethyl)-1H-indol-3-yl, or 1,2-dimethyl-1H-indol-3-yl, and more preferably 1-methyl-1H-indol-3-yl.

In another more preferred embodiment, G is pyrazolo[1,5-a]-pyridin-3-yl.

In another more preferred embodiment, G is 1-methyl-1H-indazol-3-yl.

In another embodiment of this aspect, $R^5$ is selected from the group consisting of $C_1$-$C_6$ alkyl, substituted or unsubstituted azetidinyl, substituted or unsubstituted pyrrolidinyl, substituted or unsubstituted piperidinyl, $R^7R^8N$—$(CH_2)_n$— (n is an integer selected from 1 to 5), $R^7R^8N$—$(C_3$-$C_6$ cycloalkyl)-$(CH_2)_m$— (m=1, 2, 3), wherein $R^7$ and $R^8$ are the same or different and are independently selected from hydrogen and lower alkyl.

In a preferred embodiment of this aspect, $R^5$ is selected from the group consisting of methyl, 1-(dimethylamino)-cyclopropylmethyl, 3-(dimethylamino)cyclobutyl, 1-methylazetidin-3-yl, (R)-1-methylpyrrolidin-3-yl, (S)-1-methylpyrrolidin-3-yl, and 1-methylpiperidin-4-yl, and 2-dimethylamino-ethyl.

In a more preferred embodiment, $R^5$ is 2-dimethylamino-ethyl [i.e., $(CH_3)_2NCH_2CH_2$—].

In another embodiment of this aspect, $R^1$ is hydrogen, halogen, or methyl.

In a preferred embodiment of this aspect, $R^1$ is hydrogen.

In another embodiment of this aspect, $R^2$ is hydrogen or halogen, wherein halogen is preferably F or Cl.

In another embodiment of this aspect, $R^3$ is hydrogen, F, Cl, or —$CF_3$.

In another embodiment of this aspect, $R^4$ is hydrogen.

In another embodiment of this aspect, $R^2$ is hydrogen, F, or Cl; $R^3$ is hydrogen, F, Cl, or —$CF_3$; and $R^4$ is hydrogen.

In a preferred embodiment of this aspect, $R^2$, $R^3$, and $R^4$ are all hydrogen.

In a preferred embodiment of this aspect, $R^6$ is lower alkoxy, preferably methoxy or ethoxy.

In a more preferred embodiment, $R^6$ is methoxy.

In another embodiment of this aspect, sometimes preferred, X is oxygen.

In another embodiment of this aspect, sometime preferred, X is sulfur.

In another embodiment of this aspect, sometimes preferred, X is —$CH_2$—.

As would be understood by a person skilled in the art, any plausible and structurally allowable combinations of all the embodiments or preferred embodiments disclosed herein are encompassed and hereby specifically included in the present invention.

For example, in some embodiments of this aspect, G is selected from the group consisting of 1H-indol-3-yl, 1-methyl-1H-indol-3-yl, 1-(2-fluoroethyl)-1H-indol-3-yl, 1,2-dimethyl-1H-indol-3-yl, pyrazolo[1,5-a]-pyridin-3-yl, 4,5,6,7-tetrahydropyrazolo[1,5-a]pyridin-3-yl, 1-methyl-1H-indazol-3-yl, and 2-methyl-2H-indazol-3-yl;

X is selected from the group consisting of oxygen, sulfur, and methylene;

$R^1$ is selected from the group consisting of hydrogen, halogen, methyl, trifluoromethyl, and cyano;

$R^2$, $R^3$, and $R^4$ are the same or different and are independently selected from the group consisting of hydrogen, halogen, and trifluoromethyl;

$R^5$ is selected from the group consisting of 1-(dimethylamino)-cyclopropylmethyl, 3-(dimethylamino)cyclobutyl, 1-methylazetidin-3-yl, (R)-1-methylpyrrolidin-3-yl, (S)-1-methylpyrrolidin-3-yl, and 1-methylpiperidin-4-yl, and 2-dimethylamino-ethyl; and $R^6$ is lower alkoxy.

In some preferred embodiments, G is a 1H-indol-3-yl or 1H-indazol-3-yl moiety having a formula

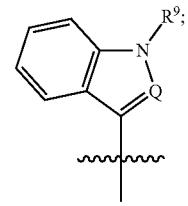

and the present invention provides a compound of formula II:

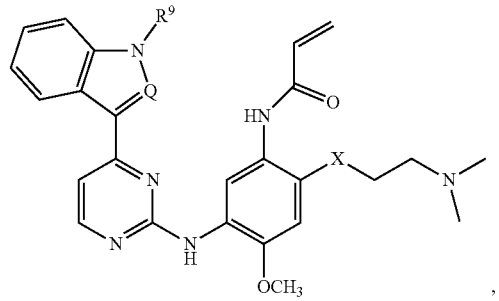

II or a pharmaceutically acceptable salt, solvate, or prodrug thereof, wherein:

X is O, S, or $CH_2$;

Q is C—$R^{10}$ or N $R^9$ is $CH_3$ or $CH_2CH_2F$; and $R^{10}$ is H or $CH_3$.

In one preferred embodiment, in formula II, Q is C—$R^{10}$, and the present invention provides a compound of formula III:

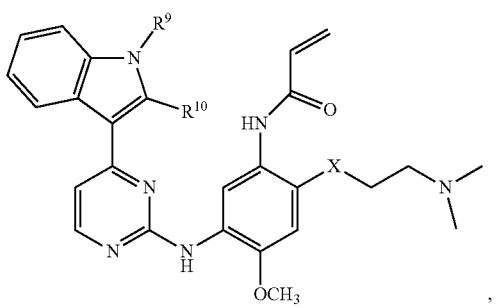

or a pharmaceutically acceptable salt, solvate, or prodrug thereof, wherein $R^9$ is $CH_3$ or $CH_2CH_2F$; and $R^{10}$ is H or $CH_3$.

In another preferred embodiment, in the compound of formula III, $R^9$ is $CH_3$ and $R^{10}$ is H.

In another preferred embodiment, in the compound of formula III, $R^9$ is $CH_3$ and $R^{10}$ is $CH_3$.

In another preferred embodiment, in the compound of formula III, $R^9$ is 2-fluoroethyl ($FCH_2CH_2-$), and $R^{10}$ is H.

In another preferred embodiment, in formula III, $R^9$ is $CH_3$, $R^{10}$ is H, and X is O, the compound having the structure of formula 1:

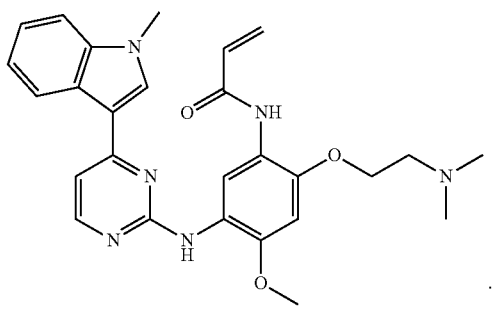

In another preferred embodiment, in formula III, $R^9$ is $CH_3$, $R^{10}$ is $CH_3$, and X is O, the compound having the structure of formula 8:

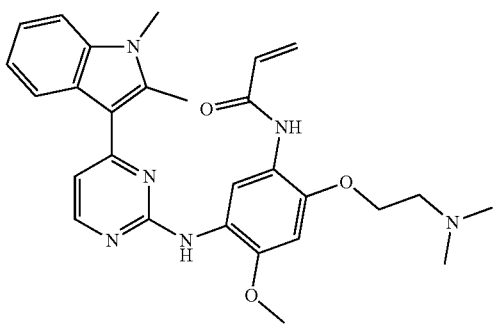

In another preferred embodiment, in formula III, $R^9$ is $CH_3$, $R^{10}$ is H, and X is S, the compound having the structure of formula 2:

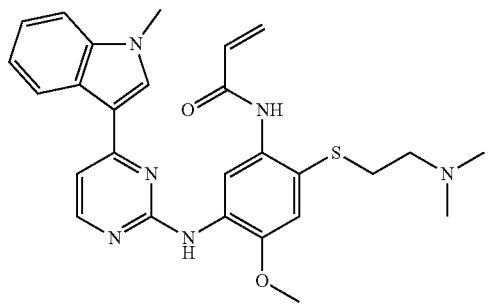

In another preferred embodiment, in formula III, $R^9$ is $CH_3$, $R^{10}$ is H, and X is $CH_2$, the compound having the structure of formula 4:

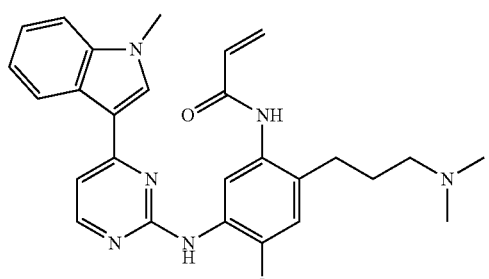

In another preferred embodiment, in formula III, $R^9$ is $-CH_2CH_2F$, $R^{10}$ is H, and X is O, the compound having the structure of formula 11:

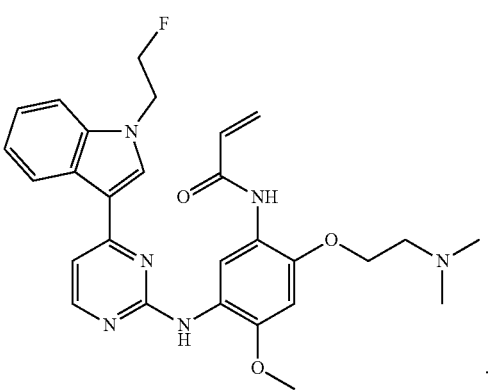

In one preferred embodiment, in formula II, Q is N, and the present invention provides a compound of formula IV:

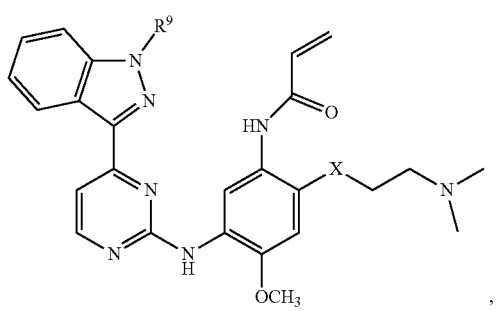

IV or a pharmaceutically acceptable salt, solvate, or prodrug thereof, wherein: $R^9$ is H or $CH_3$; and X is O, S, or $CH_2$.

In a more preferred embodiment, in formula IV, $R^9$ is H or $CH_3$, and X is O, the compound having the structure of formula 10:

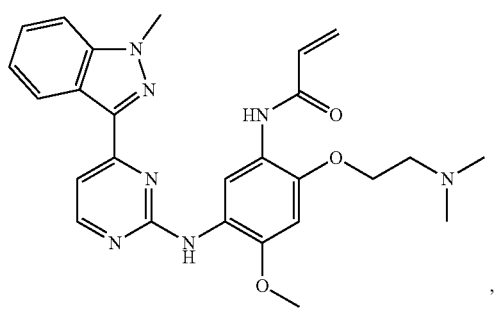

10

In some other preferred embodiments, in formula I, G is pyrazolo[1,5-a]-pyridin-3-yl, and the present invention provides a compound of formula V:

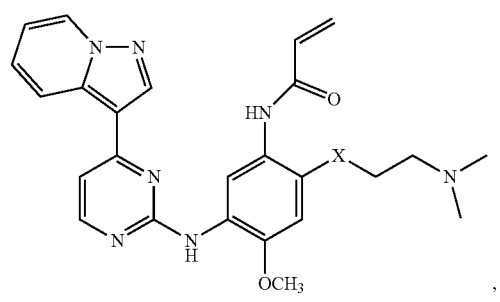

V or a pharmaceutically acceptable salt, solvate, or prodrug thereof, wherein X is O, S, or $CH_2$.

In a more preferred embodiment, in formula V, X is O, the compound having the structure of formula 9:

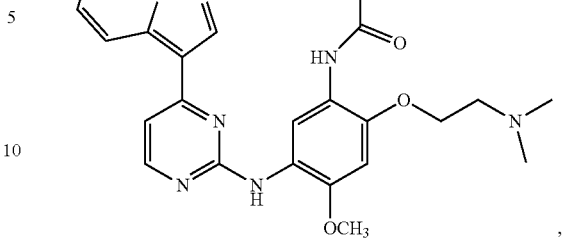

9

In some other preferred embodiments, the present invention provides a compound selected from the group consisting of the Examples listed, or a pharmaceutically acceptable salt, solvate, or prodrug thereof.

The more preferred compounds are listed below:

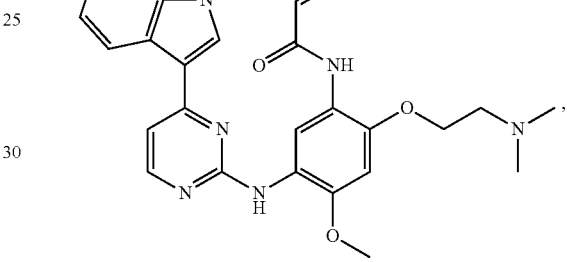

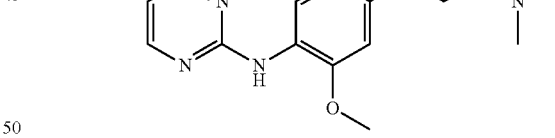

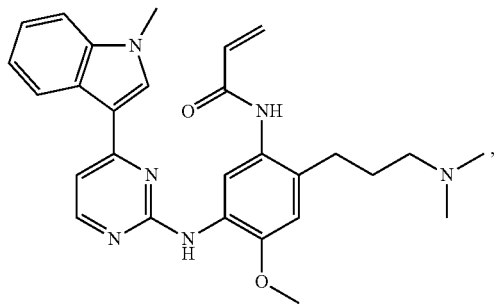

-continued

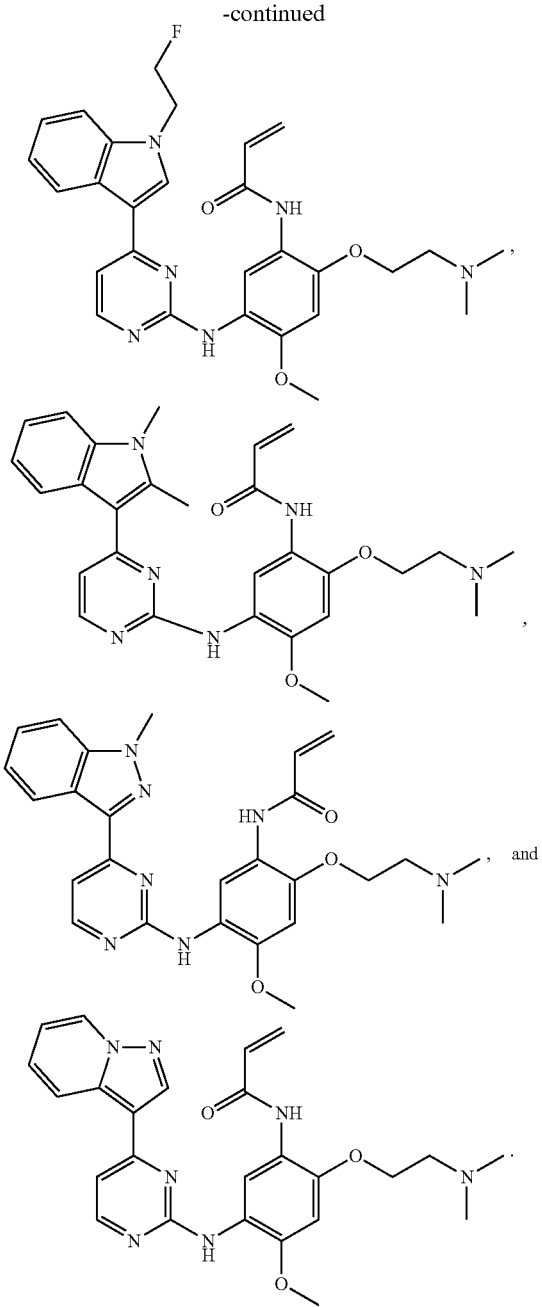

In another aspect, the present invention provides a pharmaceutical composition comprising any one of the compounds of formulas I, II, III, IV, and V, or a pharmaceutically acceptable salt, solvate, or prodrug thereof, and a pharmaceutically acceptable carrier, adjuvant, diluent, and/or vehicle.

In one embodiment of this aspect, the composition further comprises a second therapeutic agent.

In another embodiment of this aspect, the second therapeutic agent is a different EGFR modulator.

In another embodiment of this aspect, the second therapeutic agent is a chemotherapeutic agent.

In another aspect, the present invention provides a method of treating a disease or disorder associated with an EGFR activity, comprising administration of a therapeutically effective amount of a compound according to any one of formulas I, II, III, IV, and V, or a pharmaceutically acceptable salt, solvate, prodrug, or a pharmaceutical composition thereof, to a patient in need of treatment.

In one embodiment of this aspect, the disease or disorder is associated with one or more mutants of EGFR.

In another embodiment of this aspect, the mutant or mutants of EGFR are selected from L858R activating mutants L858R, delE746-A750, G719S; the Exon 19 deletion activating mutant; and the T790M resistance mutant.

In another embodiment of this aspect, the disease or disorder is a cancer.

In another embodiment of this aspect, the cancer is selected from brain cancer, lung cancer, kidney cancer, bone cancer, liver cancer, bladder cancer, head and neck cancer, esophageal cancer, stomach cancer, colon cancer, rectum cancer, breast cancer, ovarian cancer, melanoma, skin cancer, adrenal cancer, cervical cancer, lymphoma, and thyroid tumors and their complications.

In another embodiment of this aspect, the method is used in conjunction with administering to the patient a second therapeutic agent.

In another embodiment of this aspect, the second therapeutic agent is a chemotherapeutic agent.

In another embodiment of this aspect, the second therapeutic agent is a different EGFR modulator.

In another aspect, the present invention provides a method of inhibiting a mutant of EGFR in a subject, comprising contacting a biological sample of said subject with a compound of any one of formulas I, II, III, IV, and V according to any embodiment disclosed herein, or a pharmaceutically acceptable salt, solvate, or prodrug thereof. Such inhibition can be in vitro or in vivo. If in vivo, the method may comprise administering to said subject a compound of any one of formulas I, II, III, IV, and V according to any embodiment disclosed herein, or a pharmaceutically acceptable salt, solvate, or prodrug thereof. If in vitro, such inhibition may be conducted in a medium in any container known to those skilled in the art.

In another aspect, the present invention provides use of a compound of any one of formulas I, II, III, IV, and V according to any embodiment disclosed herein, or a pharmaceutically acceptable salt, solvate, or prodrug thereof, or a composition of any one of formulas I, II, III, IV, and V according to any embodiment disclosed herein, in the manufacture of a medicament for treatment of a disease or disorder associated with an EGFR activity.

In one embodiment of this aspect, disease or disorder is a cancer selected from the group consisting of brain cancer, lung cancer, kidney cancer, bone cancer, liver cancer, bladder cancer, head and neck cancer, esophageal cancer, stomach cancer, colon cancer, rectum cancer, breast cancer, ovarian cancer, melanoma, skin cancer, adrenal cancer, cervical cancer, lymphoma, and thyroid tumors and their complications. In a preferred embodiment, the cancer is brain cancer or lung cancer. The lung cancer includes, but is not limited to, non-small cell lung cancer and small cell lung cancer.

The terms in the present application, if not specifically defined, take their ordinary meanings as would be understood by those skilled in the art.

As used herein, the term "halo" or "halogen" refers to F, Cl, or Br.

The term "lower alkyl" refers to a branched or straight-chain alkyl group having from one to seven carbon atoms, preferably one to four, and more preferably one to two carbon atoms.

The term "lower alkoxy" refers to an alkoxy group (—OR) having from one to seven, preferably one to four, and more preferably one to two carbon atoms.

The term "cyano" refers to —CN.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

The term "solvate," as used herein, means a physical association of a compound of this invention with a stoichiometric or non-stoichiometric amount of solvent molecules. For example, one molecule of the compound associates with one or more, preferably one to three, solvent molecules. It is also possible that multiple (e.g., two) molecules of the compound share one solvent molecule. This physical association may include hydrogen bonding. In certain instances the solvates will be capable of isolation as crystalline solid. The solvent molecules in the solvate may be present in a regular arrangement and/or a non-ordered arrangement. Exemplary solvates include, but are not limited to, hydrates, ethanolates, methanolates, and isopropanolates. Methods of solvation are generally known in the art.

The term "prodrug," as used herein, refers to a derivative of a compound that can be transformed in vivo to yield the parent compound, for example, by hydrolysis in blood. Common examples include, but are not limited to, ester and amide forms of an active carboxylic acid compound; or vice versa, an ester from an active alcohol compound or an amide form of an active amine compound. Such amide or ester prodrug compounds may be prepared according to conventional methods as known in the art. For example, a prodrug of a compound of formula II of the present invention could be in the form of the following formula VI:

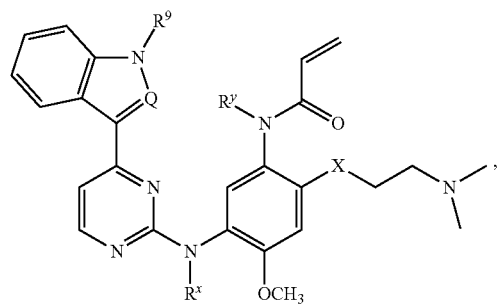

wherein $R^x$ and $R^y$ are independently H and —C(O)—R, wherein R is $C_1$-$C_4$ alkyl, preferably methyl or ethyl, and more preferably methyl. Other prodrugs of the present invention can be prepared similarly from any of formulas I, II, III, IV, and V.

When it is possible that, for use in therapy, therapeutically effective amounts of a compound of the present invention, or pharmaceutically acceptable salts or solvates thereof, may be administered as the raw chemical, it is possible to present the active ingredient as a pharmaceutical composition. Accordingly, the disclosure further provides pharmaceutical compositions, which include any compounds of the present invention, or pharmaceutically acceptable salts or solvates thereof, and one or more, preferably one to three, pharmaceutically acceptable carriers, diluents, or other excipients. The carrier(s), diluent(s), or other excipient(s) must be acceptable in the sense of being compatible with the other ingredients of the formulation and not deleterious to the subject being treated.

Pharmaceutical formulations may be presented in unit dose forms containing a predetermined amount of active ingredient per unit dose. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford effective results without causing substantial harmful or deleterious side effects.

When the compositions of this disclosure comprise a combination of a compound of the present disclosure and one or more, preferably one or two, additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example, by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection is preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

It should be understood that in addition to the ingredients particularly mentioned above, the formulations may include other agents conventional in the art having regard to the type of formulation in question, for example those suitable for oral administration may include flavoring agents.

The term "patient" or "subject" includes both human and other mammals.

The term "mammal" or "mammalian animal" includes, but is not limited to, humans, dogs, cats, horses, pigs, cows, monkeys, rabbits and mice. The preferred mammals are humans.

The term "therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, or other factors of the subject to be treated. When applied to an individual active ingredient, administered alone, the term refers to that ingredient alone. When applied to a combination, the term refers to combined amounts of the active ingredients that result in the therapeutic effect, whether administered in combination, serially, or simultaneously.

The term "treating" or "treatment" refers to: (i) inhibiting the disease, disorder, or condition, i.e., arresting its development; (ii) relieving the disease, disorder, or condition, i.e., causing regression of the disease, disorder, and/or condition; or (iii) preventing a disease, disorder or condition from occurring in a subject that may be predisposed to the disease, disorder, and/or condition but has not yet been diagnosed as having it. Thus, in one embodiment, "treating" or "treatment" refers to ameliorating a disease or disorder, which may include ameliorating one or more physical parameters, though maybe indiscernible by the subject being treated. In another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

When the term "about" is applied to a parameter, such as amount, temperature, time, or the like, it indicates that the parameter can usually vary by ±10%, preferably within ±5%, and more preferably within ±2%. As would be understood by a person skilled in the art, when a parameter is not critical, a number provided in the Examples is often given only for illustration purpose, instead of being limiting.

The term "a," "an," or "the," as used herein, represents both singular and plural forms. In general, when either a singular or a plural form of a noun is used, it denotes both singular and plural forms of the noun.

The following non-limiting Examples further illustrate certain aspects of the present invention.

EXAMPLES

Chemical Synthesis

The compounds of the present invention are prepared generally according to Synthetic Schemes 1 to 8 in the illustrative, non-limiting Examples described below.

Abbreviations

The following abbreviations may be used:
THF=Tetrahydrofuran;
conc.=concentrated
DIEA=DIPEA=Diisopropylethylamine;
sat.=saturated aqueous solution;
FCC=flash column chromatography using silica;
TFA=Trifluoroacetic acid;
r.t.=room temperature;
DI=deionized;
DME=1,2-Dimethoxyethane
DMF=N,N-Dimethylformamide;
DMSO=Dimethylsulfoxide;
DMA=N,N-Dimethylacetamide;
HATU=O-(7-Azabenzotriazol-1-yl)-N,N,N',N'-tetramethyl-uronium hexafluoro-phosphate;
EtOAc=Ethyl acetate;
h=hour(s);
NMM=N-Methylmorpholine
$Pd_2(dba)_3$=Tris(dibenzylideneacetone)dipalladium(0);
$P(o-tol)_3$=Tri(o-tolyl)phosphine.

Example 1

N-(2-(2-(Dimethylamino)ethoxy)-4-methoxy-5-((4-(1-methyl-1H-indol-3-yl)pyrimidin-2-yl)amino)phenyl)acrylamide (1)

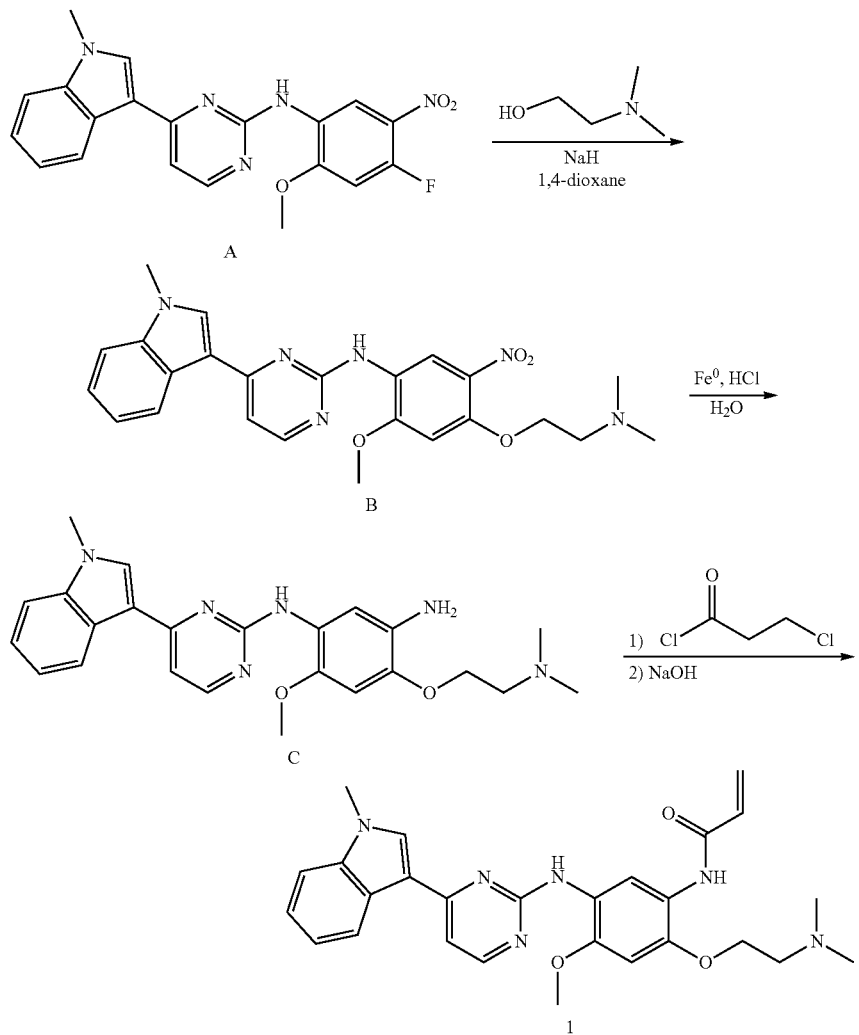

N-(4-(2-(Dimethylamino)ethoxy)-2-methoxy-5-nitrophenyl)-4-(1-methyl-1H-indol-3-yl)pyrimidin-2-amine (Scheme 1, Intermediate B). To a slurry of NaH (30 mmol, 60% oil dispersion prewashed with hexanes) and 50 mL of 1,4-dioxane was added 2-dimethylaminoethanol (27 mmol, 2.7 mL) dropwise with stirring under $N_2$. After stirring for 1 h, a slurry of A (5.4 mmol) in 50 mL of 1,4-dioxane was added portion-wise over 15 min under a stream of $N_2$. The resulting mixture was stirred overnight, then poured into water and the solid was collected, rinsed with water, and dried under vacuum to yield 2.6 g of product as a yellow solid. A purified sample was obtained from chromatography (silica gel; $CH_2Cl_2$—$CH_3OH$ gradient). $^1$H NMR (300 MHz, DMSO) δ 2.26 (s, 6H), 2.70 (t, 2H, J=6 Hz), 3.87 (s, 3H), 4.01 (s, 3H), 4.32 (t, 2H, J=6 Hz), 7.00-7.53 (m, 5H), 8.18-8.78 (m, 5H); $C_{24}H_{26}N_6O_4$ m/z MH$^+$ 463.

4-(2-(Dimethylamino)ethoxy)-6-methoxy-N1-(4-(1-methyl-1H-indol-yl)pyrimidin-2-yl)benzene-1,3-diamine (Scheme 1, Intermediate C). A suspension of 2.6 g of Intermediate B, 1.6 g of $Fe^0$, 30 mL of ethanol, 15 mL of water, and 20 mL of conc. HCl was heated to 78° C. for 3 h. The solution was cooled to room temperature, adjusted to pH 10 with 10% NaOH (aq) and diluted with $CH_2Cl_2$. The mixture was filtered through Dicalite, and the filtrate layers were separated. The aqueous phase was extracted with $CH_2Cl_2$ twice, and the combined organic extracts were dried over $Na_2SO_4$ and concentrated. Column chromatography (silica gel, $CH_2Cl_2$—MeOH gradient) afforded 1.2 g of Intermediate C as a solid. $C_{24}H_{28}N_6O_2$ m/z MH$^+$ 433.

N-(2-(2-(Dimethylamino)ethoxy)-4-methoxy-5-((4-(1-methyl-1H-indol-3-yl)pyrimidin-2-yl)amino)phenyl)acrylamide (1). To a solution of Intermediate C (2.8 mmol) in 50 mL of THF and 10 mL of water was added 3-chloropropionychloride (2.8 mmol) dropwise with stirring. After 5 h of stirring, NaOH (28 mmol) was added and the mixture was heated at 65° C. for 18 h. After cooling to room temperature, THF was partially removed under reduced pressure, and the mixture was extracted with $CH_2Cl_2$, dried over $Na_2SO_4$, and concentrated. Chromatography of the crude product (silica gel, $CH_2Cl_2$-MeOH) afforded 0.583 g of Example 1 as a beige solid. $^1$H NMR (300 MHz, DMSO) δ 2.28 (s, 6H), 2.50-2.60 (m, 2H), 3.86 (s, 3H), 3.90 (s, 3H), 4.19 (t, 2H, J=5.5 Hz), 5.73-5.77 (m, 1H), 6.21-6.27 (m, 1H), 6.44-6.50 (m, 1H), 6.95 (s, 1H), 7.11-7.53 (overlapping m, 3H), 7.90 (s, 1H), 8.27-8.30 (overlapping m, 3H), 8.55 (s, 1H), 8.84 (s, 1H), 9.84 (s, 1H) ppm; $C_{27}H_{30}N_6O_3$ m/z MH$^+$ 487.

Example 2

N-(2-((2-(Dimethylamino)ethyl)thio)-4-methoxy-5-((4-(1-methyl-1H-indol-3-yl)pyrimidin-2-yl)amino)phenyl)acrylamide (2)

Scheme 2

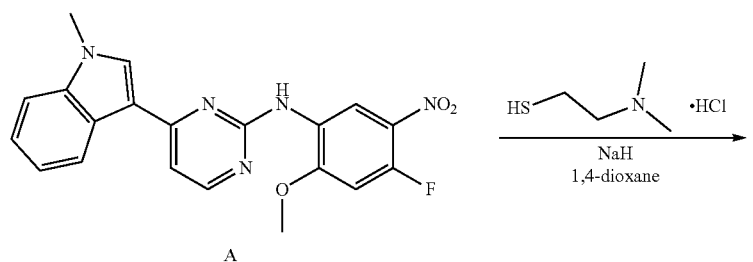

A

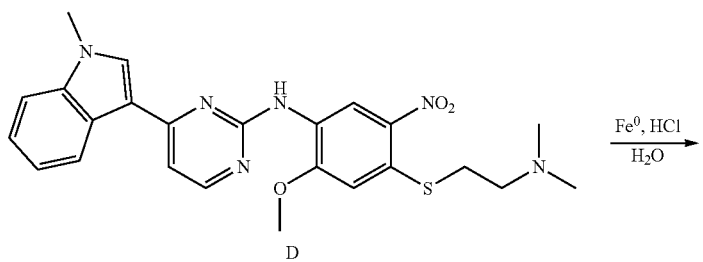

D

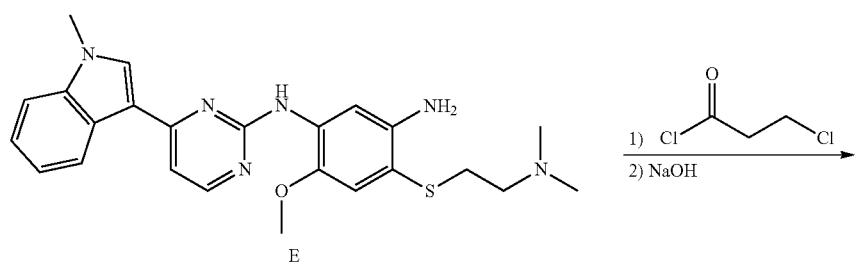

E

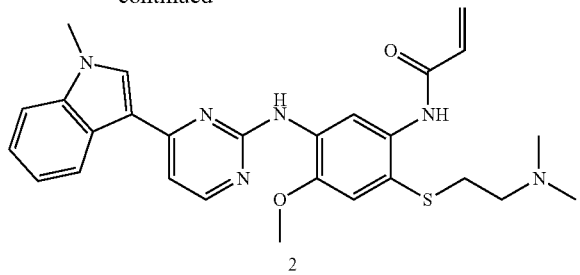

2

N-(4-((2-(Dimethylamino)ethyl)thio)-2-methoxy-5-nitrophenyl)-4-(1-methyl-1H-indol-3-yl)pyrimidin-2-amine (Scheme 2, Intermediate D). To a slurry of NaH (54 mmol, 60% oil dispersion prewashed with hexanes) and 25 mL of DMF was added a slurry of 2-dimethylaminoethanethiol hydrochloride (27 mmol) in 25 mL of DMF under a stream of $N_2$. After stirring for 45 min, a slurry of A (5.4 mmol) in 25 mL of DMF was added portionwise over 15 min to the mixture under a stream $N_2$. The resulting mixture was stirred overnight, then poured into water and the solid was collected, rinsed repeatedly with water, and dried under vacuum to yield 2.5 g of product as a yellow solid. $C_{24}H_{26}N_6O_3S$ m/z MH+ 479.

4-((2-(Dimethylamino)ethyl)thio)-6-methoxy-$N^1$-(4-(1-methyl-1H-indol-3-yl)pyrimidin-2-yl)benzene-1,3-diamine (Scheme 2, Intermediate E). A suspension of 2.5 g of Intermediate D, 3.0 g of Fe⁰, 50 mL of ethanol, 20 mL of water, and 7 mL of conc. HCl was heated to 78° C. for 3 h. The solution was cooled to room temperature, adjusted to pH 10 with 10% NaOH (aq), and diluted with $CH_2Cl_2$. The mixture was filtered through Dicalite, and the filtrate layers were separated. The aqueous phase was extracted with $CH_2Cl_2$ twice, and the combined organic extracts were dried over $Na_2SO_4$ and concentrated. Column chromatography (silica gel, $CH_2Cl_2$-MeOH gradient) afforded 1.2 g of Intermediate E as a solid. $C_{24}H_{28}N_6OS$ m/z MH+ 449.

N-(2-((2-(Dimethylamino)ethyl)thio)-4-methoxy-5-((4-(1-methyl-1H-indol-3-yl)pyrimidin-2-yl)amino)phenyl)acrylamide (2). To a solution of Intermediate E (2.7 mmol) in 50 mL of THF and 10 mL of water was added 3-chloropropionychloride (4.0 mmol) dropwise with stirring. After 2 h of stirring, NaOH (27 mmol) was added and the mixture was heated at 65° C. for 18 h. After cooling to room temperature, THF was partially removed under reduced pressure, and the mixture was extracted with $CH_2Cl_2$, dried over $Na_2SO_4$, and concentrated. Chromatography of the crude product (silica gel, $CH_2Cl_2$-MeOH—$NH_4OH$ gradient) afforded 0.622 g of Example 2 as an off-white solid: $^1$H NMR (300 MHz, DMSO) δ 2.19 (s, 6H), 2.34 (t, 2H, J=6.5 Hz), 2.98 (t, 2H, J=6.5 Hz), 3.91 (s, 3H), 3.93 (s, 3H), 5.50-6.57 (overlapping m, 3H), 7.12-9.88 (overlapping m, 10H), 10.17 (s, 1H) ppm. $C_{27}H_{30}N_6O_2S$ m/z MH+ 503.

Example 3

N-(2,4-Dimethoxy-5-((4-(1-methyl-1H-indol-yl)pyrimidin-2-yl)amino)-phenyl)acrylamide (3)

Scheme 3

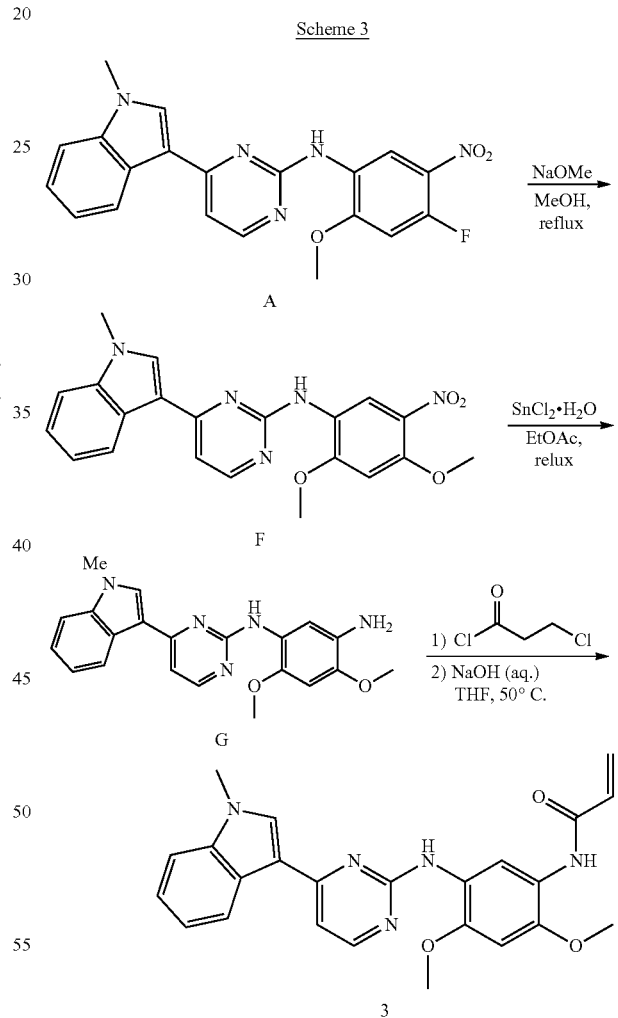

3

N-(2,4-Dimethoxy-5-nitrophenyl)-4-(1-methyl-1H-indol-3-yl)pyrimidin-2-amine (Scheme 3, Intermediate F). Sodium methoxide, 25 wt. % solution in methanol (40 mL, 175 mmol), was slowly poured into a stirred, ambient temperature, suspension of N-(4-fluoro-2-methoxy-5-nitrophenyl)-4-(1-methyl-1H-indol-3-yl)pyrimidin-2-amine (Scheme 1, Intermediate A; 5.8 g, 14.7 mmol) in methanol (125 mL) and heated at reflux for 4 days under nitrogen blanket, during which time the solid did not dissolve. The reaction was cooled, product precipitate isolated by filtration, washed with cold methanol, and dried to yield 5.45 g of N-(2,4-dimethoxy-5-nitrophenyl)-4-(1-methyl-1H-indol-3-yl)pyrimidin-2-amine (Intermediate F) as a yellow powder. $C_{21}H_{19}N_5O_4$ m/z MH+ 406.

4,6-Dimethoxy-$N^1$-(4-(1-methyl-1H-indol-3-yl)pyrimidin-2-yl)benzene-1,3-diamine (Scheme 3, Intermediate G). Stannous chloride dihydrate (8.9 g, 39.4 mmol) was added to a stirred, ambient temperature suspension of N-(2,4-dimethoxy-5-nitrophenyl)-4-(1-methyl-1H-indol-3-yl)pyrimidin-2-amine (Intermediate F; 3.2 g, 7.9 mmol) in ethyl acetate (200 mL) and heated at reflux under nitrogen blanket for 3 h. The reaction was allowed to cool, then poured into a 5% (w/v) solution of sodium bicarbonate in DI water (400 mL) and stirred for 1 h. The multiphase mixture was then filtered through tightly packed Celite, with ethyl acetate rinsing of the filter cake. The filtrate was transferred to a separatory funnel and the liquid phases separated. The retained ethyl acetate solution of product was washed with brine and dried over anhydrous calcium sulfate. Filtration and evaporation yielded 1.6 g of crude product. Purification by gradient flash chromatography ($SiO_2$, 0 to 70% hexanes/ethyl acetate over 20 min.) provided 0.9 g of 4,6-dimethoxy-$N^1$-(4-(1-methyl-1H-indol-3-yl)pyrimidin-2-yl)benzene-1,3-diamine (Intermediate G) as a yellow foam. $C_{21}H_{21}N_5O_2$ m/z MH+ 376.

N-(2,4-Dimethoxy-5-((4-(1-methyl-1H-indol-3-yl)pyrimidin-2-yl)amino)phenyl)acrylamide (3). 3-Chloropropanoyl chloride (90 µL, 0.92 mmol) was rapidly added by syringe to a rapidly stirred, ambient temperature, nitrogen blanketed solution of 4,6-dimethoxy-$N^1$-(4-(1-methyl-1H-indol-3-yl)pyrimidin-2-yl)benzene-1,3-diamine (Intermediate G; 351 mg, 0.94 mmol) and N-methylmorpholine (0.11 mL, 1.0 mmol) in ethyl acetate (9.4 mL), precipitate immediately formed, and reaction was allowed to proceed for 40 min., evaporated to dryness, and dissolved in 10% (v/v) DI water/tetrahydrofuran. Solid sodium hydroxide (3 g, 75 mmol) was added and the stirred mixture heated to 50° C. for 17 h. The reaction solution was cooled, partitioned between brine and ethyl acetate. The ethyl acetate phase was dried over anhydrous calcium sulfate, filtered, and then chilled in an ice bath with stirring while slowly being diluted with hexanes to precipitate the product. This material was isolated by filtration and dried to provide 189 mg of Example 3 as fine light-yellow powder. $^1$H NMR (300 MHz, DMSO) δ 3.88 (s, 6H), 3.90 (s, 3H), 5.70 (dd, 1H, J=10.15, 1.92 Hz), 6.22 (dd, 1H, J=16.95, 2.03 Hz), 6.70 (q, 1H, J=9.06 Hz), 6.85 (s, 1H), 7.11-7.17 (m, 2H), 7.23 (t, 1H, J=6.96 Hz), 7.50 (d, 1H, J=8.23 Hz), 7.93 (s, 1H), 8.28 (m, 2H), 8.47 (s, 1H), 8.67 (s, 1H), 9.38 (s, 1H) ppm. $^{13}$C NMR (75 MHz, DMSO) δ 33.4, 56.5, 56.7, 97.3, 107.1, 110.8, 113.0, 118.5, 119.5, 121.3, 121.5, 122.3, 122.5, 125.9, 126.4, 132.8, 133.8, 138.1, 147.3, 148.3, 157.8, 160.8, 162.3, 163.5 ppm. $C_{24}H_{23}N_5O_3$ m/z MH+ 430.

Example 4

N-(2-(3-(Dimethylamino)propyl)-4-methoxy-5-((4-(1-methyl-1H-indol-3-yl)pyrimidin-2-yl)amino)phenyl)acrylamide (4)

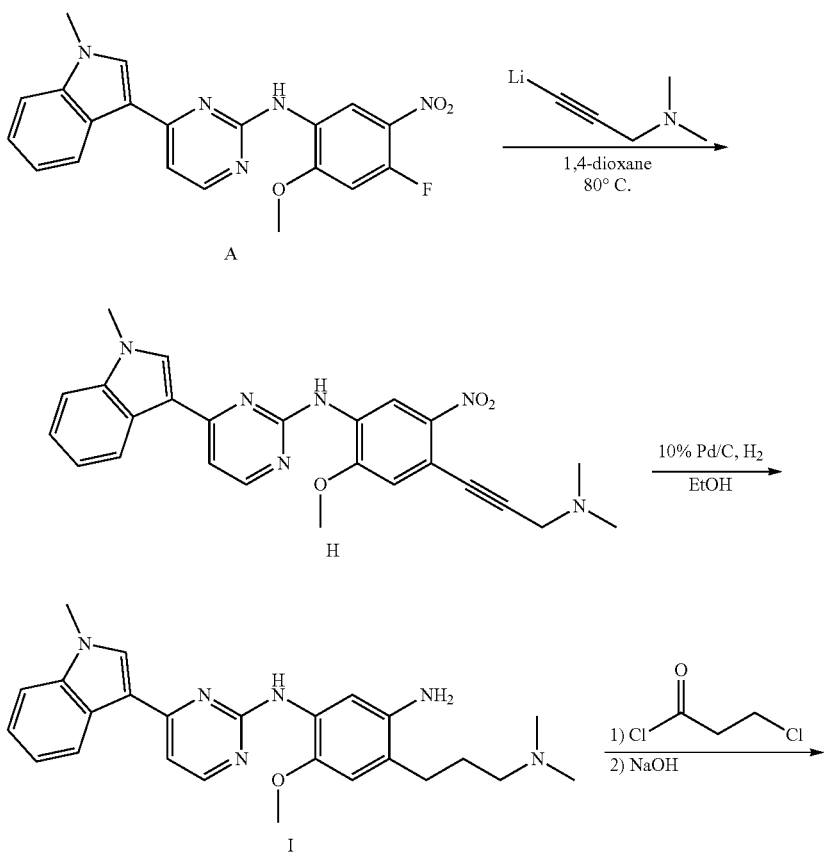

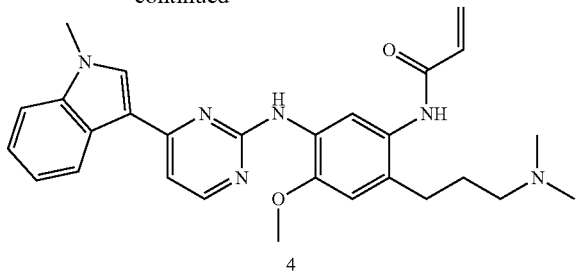

N-(4-(3-(Dimethylamino)prop-1-yn-1-yl)-2-methoxy-5-nitrophenyl)-4-(1-methyl-1H-indol-3-yl)pyrimidin-2-amine (Scheme 4, Intermediate H). A solution of 3-dimethylamino-1-propyne (1.37 mL, 12.7 mmol) in 1,4-dioxane (60 mL) was treated with 1 M lithium bis(trimethylsilyl)amide (12.7 mL, 12.7 mmol) and stirred for 30 min at RT under a nitrogen atmosphere. The resulting reaction mixture, which appeared as a white slurry, was treated with N-(4-fluoro-2-methoxy-5-nitrophenyl)-4-(1-methyl-1H-indol-3-yl)pyrimidin-2-amine (Intermediate A; 1.00 g, 2.54 mmol) in one portion and heated at 80° C. while vigorously stirring under nitrogen for 5 h. The reaction mixture was cooled to RT, quenched by the addition of 10 mL of water and subsequently concentrated in vacuo. The residue was partitioned between water (100 mL) and $CH_2Cl_2$ (50 mL). The basic aqueous layer was extracted with $CH_2Cl_2$ (2×50 mL) and the combined organic extracts were washed with brine (2×50 mL), dried ($Na_2SO_4$), filtered and concentrated in vacuo to furnish 1.0 g of the crude product as a dark reddish-brown solid. This material was purified by gradient flash chromatography on $SiO_2$ eluting with 0 to 10% methanol (containing 2% $NH_4OH$) in $CH_2Cl_2$ over 60 min to afford 98 mg of N-(4-(3-(dimethylamino)prop-1-yn-1-yl)-2-methoxy-5-nitrophenyl)-4-(1-methyl-1H-indol-3-yl)pyrimidin-2-amine (Intermediate H) as an orange solid. $C_{25}H_{24}N_6O_3$ m/z MH$^+$ 457.

4-(3-(Dimethylamino)propyl)-6-methoxy-$N^1$-(4-(1-methyl-1H-indol-3-yl)pyrimidin-2-yl)benzene-1,3-diamine (Scheme 4, Intermediate I). 10% Pd/C (10 mg) was added under a nitrogen atmosphere to a solution of N-(4-(3-(dimethylamino)prop-1-yn-1-yl)-2-methoxy-5-nitrophenyl)-4-(1-methyl-1H-indol-3-yl)pyrimidin-2-amine (Intermediate H; 50 mg, 0.109 mmol) in 10 mL of THF/methanol (1:1). A hydrogen-filled balloon was connected to the reaction vessel and the reaction was stirred at RT under a hydrogen atmosphere for 6 h. The reaction mixture was filtered through Celite 545 and concentrated in vacuo to give 50 mg of crude product. This material was purified by gradient flash chromatography on $SiO_2$ eluting with 0 to 10% methanol (containing 2% $NH_4OH$) in $CH_2Cl_2$ over 50 min to afford 34 mg of 4-(3-(dimethylamino)propyl)-6-methoxy-$N^1$-(4-(1-methyl-1H-indol-3-yl)pyrimidin-2-yl)benzene-1,3-diamine (Intermediate I) as a foam. $C_{25}H_{30}N_6O$ m/z MH$^+$ 431.

N-(2-(3-(Dimethylamino)propyl)-4-methoxy-5-((4-(1-methyl-1H-indol-3-yl)pyrimidin-2-yl)amino)phenyl)acrylamide (4). 3-Chloropropanoyl chloride (18.2 µL, 0.190 mmol) was rapidly added to a solution of 4-(3-(dimethylamino)propyl)-6-methoxy-$N^1$-(4-(1-methyl-1H-indol-3-yl)pyrimidin-2-yl)benzene-1,3-diamine (Intermediate I; 34 mg, 0.079 mmol) in 3.2 mL of THF/water (9:1) while stirring under nitrogen at RT. After 3 h, 1M aq NaOH (0.79 mL, 0.79 mmol) and the reaction mixture was heated at 65° C. for 17 h. The reaction mixture was cooled to RT, diluted with water (15 mL) and the resulting light gray precipitate was isolated by filtration to give 31 mg of crude product. This material was purified by gradient flash chromatography on $SiO_2$ eluting with 0 to 10% methanol (containing 2% $NH_4OH$) in $CH_2Cl_2$ over 35 min to afford 22 mg of Example 4 as an off-white solid. $^1$H NMR (300 MHz, CDCl$_3$) δ 1.81-1.92 (m, 2H), 2.16 (t, 2H, J=5.9 Hz), 2.27 (s, 6H), 2.69 (t, 2H, J=6.3 Hz), 3.89 (s, 3H), 3.98 (s, 3H), 5.71 (dd, 1H, J=10.1, 1.9 Hz), 6.25 (dd, 1H, J=16.9, 10.1 Hz), 6.48 (dd, 1H, J=16.9, 1.9 Hz), 6.66 (s, 1H), 7.17 (d, 1H, J=5.3 Hz), 7.22-7.43 (m, 3H), 7.72 (s, 1H), 8.05-8.12 (m, 1H), 8.37 (d, 1H, J=5.3 Hz), 8.85 (s, 1H), 9.33 (s, 1H), 10.95, (br s, 1H); $C_{28}H_{32}N_6O_2$ m/z MH$^+$ 485.

Examples 5, 6, and 7

Scheme 5

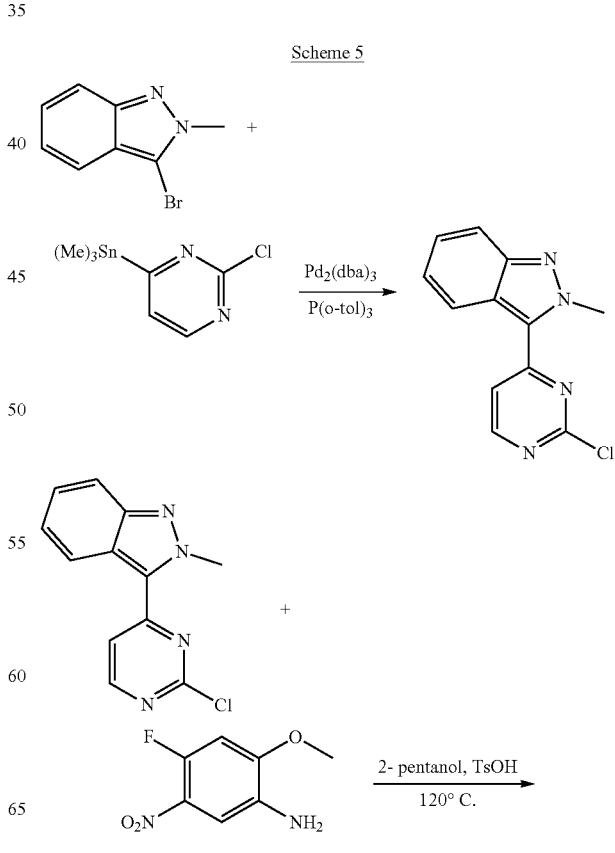

-continued

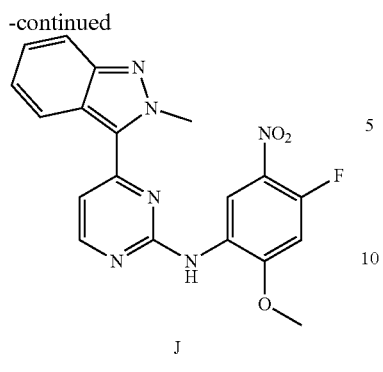

J

N-(2-(2-(Dimethylamino)ethoxy)-4-methoxy-5-((4-(2-methyl-2H-indazol-3-yl)pyrimidin-2-yl)amino)phenyl)acrylamide (5)

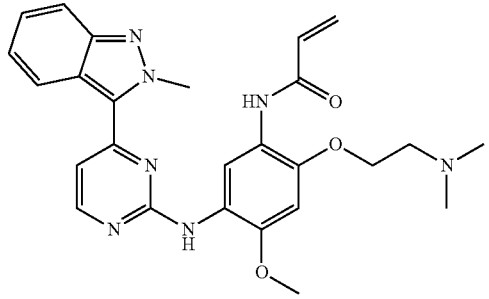

N-(2-((2-(Dimethylamino)ethyl)thio)-4-methoxy-5-((4-(2-methyl-2H-indazol-3-yl)pyrimidin-2-yl)amino)phenyl)acrylamide (6)

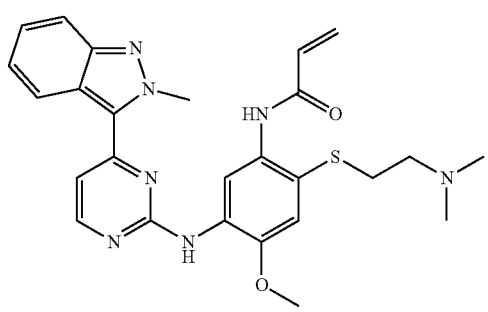

N-(2,4-Dimethoxy-5-(((4-(2-methyl-2H-indazol-3-yl)pyrimidin-2-yl)amino)phenyl)acrylamide (7)

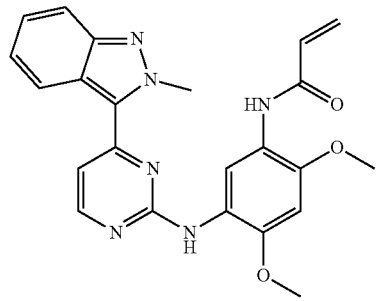

The synthesis of N-(4-fluoro-2-methoxy-5-nitrophenyl)-4-(2-methyl-2H-indazol-3-yl)pyrimidin-2-amine (Intermediate J) is shown above in Scheme 5. Examples 5, 6, and 7 are prepared as in Schemes 1, 2, and 3, respectively, by substituting Intermediate J for Intermediate A in each of those schemes.

Example 8

N-(5-((4-(1,2-Dimethyl-1H-indol-3-yl)pyrimidin-2-yl)amino)-2-(2-(dimethylamino)ethoxy)-4-methoxyphenyl)acrylamide (8)

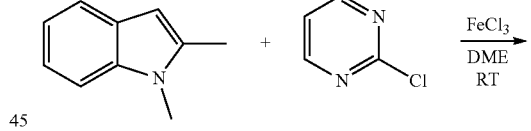

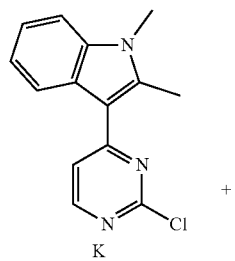

K

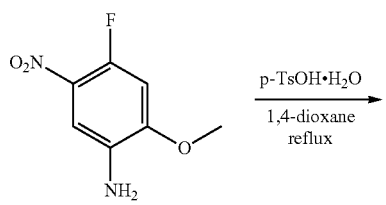

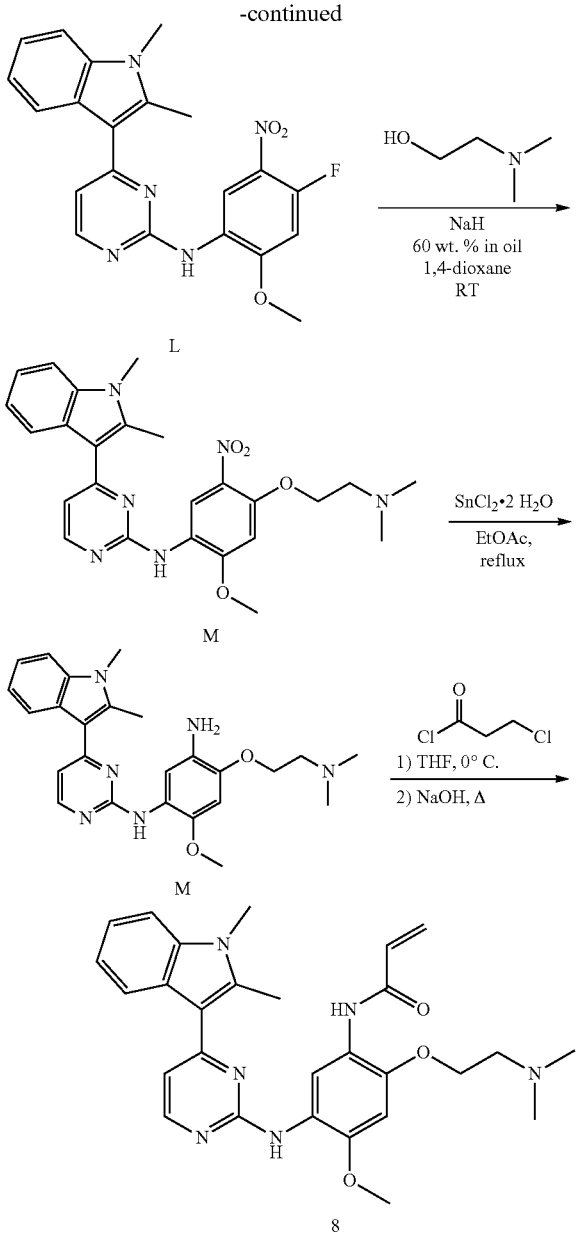

Hz), 8.10 (d, 1H, J=7.46 Hz), 8.61 (d, 1H, J=5.43 Hz) ppm. $^{13}$C NMR (75 MHz, DMSO) δ 12.8, 30.3, 108.8, 110.8, 117.5, 120.0, 121.8, 122.5, 125.8, 137.4, 142.6, 159.8, 160.4, 165.2 ppm. $C_{14}H_{12}ClN_3$ m/z MH$^+$ 258.

4-(1,2-Dimethyl-1H-indol-3-yl)-N-(4-fluoro-2-methoxy-5-nitrophenyl)-pyrimidin-2-amine (Scheme 6, Intermediate L). Reagent grade 1,4-dioxane (57 mL) was added to a mixture of 3-(2-chloropyrimidin-4-yl)-1,2-dimethyl-1H-indole (1.47 g, 5.70 mmol), 4-fluoro-2-methoxy-5-nitroaniline (1.06 g, 5.69 mmol), and p-toluenesulfonic acid monohydrate (1.31 g, 6.89 mmol) contained in a 100 mL round bottom flask fitted with a reflux condenser and blanketing nitrogen inlet. The magnetically stirred suspension was heated to reflux under nitrogen blanket. While approaching reflux temperature the suspended solid dissolved. Reflux was continued overnight, then the reaction was cooled and poured into rapidly stirring DI water (250 mL) to precipitate the product. Crude product was isolated by filtration, washed with water and recrystallized from boiling 2-propanol to yield 2.06 g of 4-(1,2-dimethyl-1H-indol-3-yl)-N-(4-fluoro-2-methoxy-5-nitrophenyl)-pyrimidin-2-amine (Intermediate L) as a fine yellow powder. $^1$H NMR (300 MHz, DMSO) δ 2.71 (s, 3H), 3.78 (s, 3H), 4.01 (s, 3H), 7.10-7.20 (m, 3H), 7.41 (d, 1H, J=13.4 Hz), 7.55 (d, 1H, J=7.99 Hz), 7.98 (d, 1H, J=7.90 Hz), 8.44 (d, 1H, J=5.70 Hz), 8.83 (br s, 1H), 8.93 (d, 1H, J=8.38 Hz). $C_{21}H_{18}FN_5O_3$ m/z MH$^+$ 408.

4-(1,2-Dimethyl-1H-indol-3-yl)-N-(4-(2-(dimethylamino)ethoxy)-2-methoxy-5-nitrophenyl) pyrimidin-2-amine (Scheme 6, Intermediate M). 2-Dimethylaminoethanol (0.43 mL, 4.27 mmol) was added, by syringe over 5 min., to a stirred suspension of 60 wt. % sodium (173 mg, 4.33 mmol) in anhydrous 1,4-dioxane at the ambient temperature. Gas evolution was readily observed. After ten min., with no further observable gas evolution, 4-(1,2-dimethyl-1H-indol-3-yl)-N-(4-fluoro-2-methoxy-5-nitrophenyl)-pyrimidin-2-amine (Intermediate J) (351 mg, 0.86 mmol) was added, neat, to the rapidly stirred pot as one bolus. The reaction suspension immediately changed to a turbid red-brown color. After 5 min. an aliquot of the reaction was withdrawn, quenched into DI water, and extracted into ethyl acetate. Analysis of this extract by UHPLC-MS revealed the reaction to be complete. The pot contents were then poured into a stirred solution of ammonium chloride (0.23 g, 4.30 mmol) in DI water (150 mL) to precipitate the product. The yellow precipitate was isolated by filtration, washed with DI water, and allowed to dry to afford 386 mg of 4-(1,2-dimethyl-1H-indol-3-yl)-N-(4-(2-(dimethylamino)ethoxy)-2-methoxy-5-nitrophenyl) pyrimidin-2-amine (Intermediate M). $C_{25}H_{28}N_6O_4$ m/z MH$^+$=477.

$N^1$-(4-(1,2-Dimethyl-1H-indol-3-yl)pyrimidin-2-yl)-4-(2-(dimethylamino)-ethoxy)-6-methoxybenzene-1,3-diamine (Scheme 6, Intermediate N). Stannous chloride dihydrate (1.73 g, 7.67 mmol) was added to a stirred suspension of 4-(1,2-dimethyl-1H-indol-3-yl)-N-(4-(2-(dimethylamino)ethoxy)-2-methoxy-5-nitrophenyl) pyrimidin-2-amine (Intermediate M; 386 mg, 0.81 mmol) in ethyl acetate (40 mL) at the ambient temperature, and the mixture was heated at reflux under nitrogen blanket for 17 h. The reaction was allowed to cool, then poured into a 1% (w/v) solution of sodium hydroxide in DI water (200 mL) and stirred for 1 h. The multiphase mixture was filtered through tightly-packed Celite, with ethyl acetate rinsing of the filter cake. The filtrate was transferred to a separatory funnel and the liquid phases were separated. The retained ethyl acetate solution of product was washed with brine, dried over anhydrous calcium sulfate, filtered and evaporated to provide a brown solid foam which was purified by gradient flash 3-(2-Chloropyrimidin-4-yl)-1,2-dimethyl-1H-indole (Scheme 6, Intermediate K). Ferric chloride (5.8 g, 34.7 mmol) was rapidly added to a degassed, clear yellow solution of 1,2-dimethyl-1H-indole (4.9 g, 33.8 mmol) and 2,4-dichloropyrimidine (5.2 g, 33.9 mmol) dissolved in anhydrous 1,2-dimethoxyethane (100 mL) while stirring at the ambient temperature. The resultant black, opaque solution was stirred at ambient temperature for 3 h under dry nitrogen atmosphere, then slowly poured into rapidly stirred 5% (w/v) aqueous NaHCO$_3$ (400 mL). Crude product was isolated by filtration, and washed with DI water on the filter. The precipitate was suspended in methanol (200 mL) and evaporated to dryness to remove excess water, then triturated in hot acetonitrile, allowed to cool, and filtered to isolate 6.2 g of 3-(2-chloropyrimidin-4-yl)-1,2-dimethyl-1H-indole (Intermediate K) as a brown powder. $^1$H NMR (300 MHz, DMSO) δ 2.77 (s, 3H), 3.79 (s, 3H), 7.23 (quin, 2H, J=7.53 Hz), 7.57 (d, 1H, J=7.25 Hz), 7.72 (d, 1H, J=5.61 chromatography (SiO$_2$, 2% NH$_4$OH in MeOH/ethyl acetate, 0 to 20% over 40 min.) to provide 186 mg of N$^1$-(4-(1,2-dimethyl-1H-indol-3-yl)pyrimidin-2-yl)-4-(2-(dimethyl-amino)-ethoxy)-6-methoxybenzene-1,3-diamine (Intermediate N) as yellow solid. $^1$H NMR (300 MHz, DMSO) δ 2.34 (s, 6H), 2.70 (t, 2H, J=6.90 Hz), 2.75 (s, 3H), 3.58 (br s, 2H), 3.74 (s, 3H), 3.83 (s, 3H), 4.07 (t, 2H, J=5.34 Hz), 6.57 (s, 1H), 6.95 (d, 1H, J=5.19 Hz), 7.17-7.27 (m, 2H), 7.32-7.35 (m, 1H), 7.55 (s, 1H), 8.09 (dd, 1H, J=6.96, 1.77 Hz), 8.18 (s, 1H), 8.38 (d, 1H, J=5.22 Hz) ppm. C$_{25}$H$_{30}$N$_6$O$_2$ m/z MH$^+$=447.

N-(5-((4-(1,2-Dimethyl-1H-indol-3-yl)pyrimidin-2-yl)amino)-2-(2-(dimethyl-amino)ethoxy)-4-methoxyphenyl)acrylamide (8). N$^1$-(4-(1,2-Dimethyl-1H-indol-3-yl)pyrimidin-2-yl)-4-(2-(dimethylamino)ethoxy)-6-methoxy-benzene-1,3-diamine (Scheme 6, Intermediate N) is converted into Example 8 by reaction with 3-chloropropionychloride followed by treatment with NaOH by using the procedures described in the preparation of Example 1.

Example 9

N-(2-(2-(Dimethylamino)ethoxy)-4-methoxy-5-((4-(pyrazolo[1,5-a]pyridin-3-yl)pyrimidin-2-yl)amino)phenyl)acrylamide (9)

N-(4-(2-(Dimethylamino)ethoxy)-2-methoxy-5-nitrophenyl)-4-(pyrazolo[1,5-a]pyridin-3-yl) pyrimidin-2-amine (Scheme 7, Intermediate P). To a slurry of NaH (21 mmol, 60% oil dispersion prewashed with hexanes) and 20 mL of 1,4-dioxane was added 2-dimethylaminoethanol (20 mmol, 2.4 mL) dropwise with stirring under N$_2$. After stirring for 45 min, a slurry of compound O (7.9 mmol) was added portion-wise, with stirring and under a stream of N$_2$. The resulting mixture was stirred overnight, then poured into water and the solid was collected, rinsed with water, and dried under vacuum to yield 1.7 g of Intermediate P as a yellow solid, which was used in the next step without further purification: C$_{22}$H$_{23}$N$_7$O$_4$ m/z MH$^+$450.

4-(2-(Dimethylamino)ethoxy)-6-methoxy-N1-(4-(pyrazolo[1,5-a]pyridin-3-yl)benzene)-1,3-diamine (Scheme 9, Intermediate Q). A suspension of 0.7 g of Intermediate P, 0.9 g of Fe$^0$, 7 mL of ethanol, 3 mL of water, and 2 mL of glacial acetic acid was heated to 78° C. for 1 h. The solution was cooled to room temperature, filtered through Dicalite, adjusted to pH 10 with 1 N NaOH (aq) and diluted with CH$_2$Cl$_2$. The filtrate layers were separated, and the aqueous phase was extracted with CH$_2$Cl$_2$ twice, and the combined organic extracts were dried over Na$_2$SO$_4$ and concentrated. Column chromatography (silica gel, CH$_2$Cl$_2$-MeOH gradient) afforded 0.28 g of Intermediate Q as tan solid. C$_{22}$H$_{25}$N$_7$O$_2$ m/z MH$^+$ 420.

Scheme 7

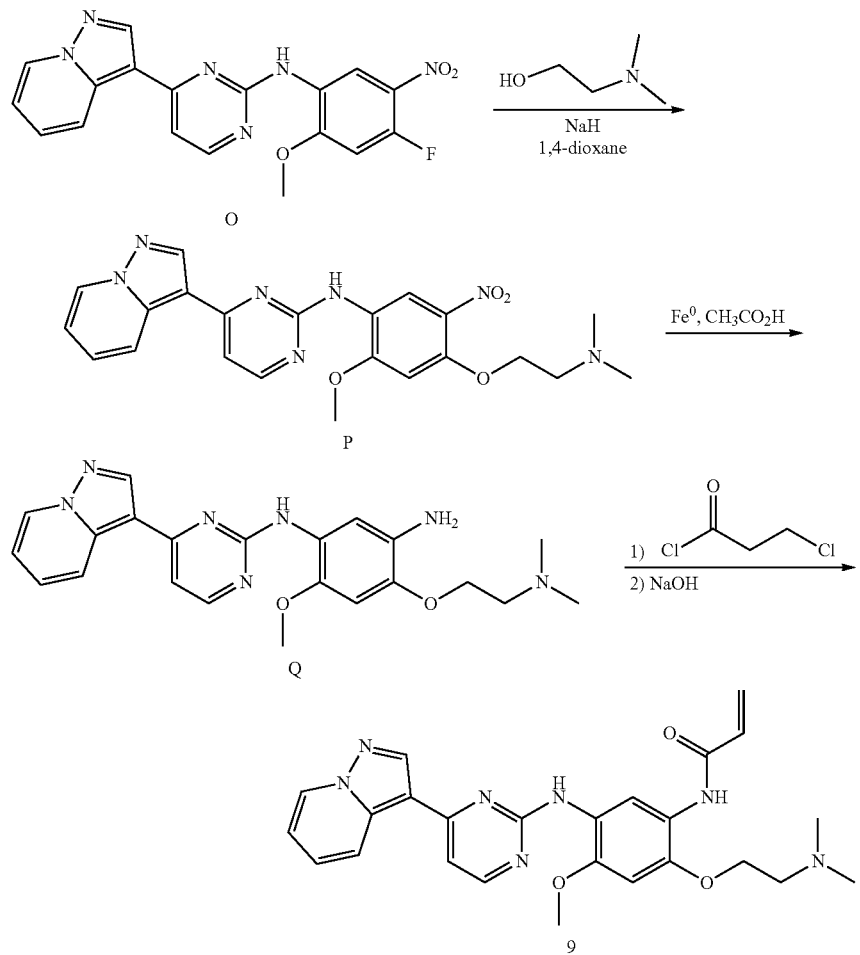

N-(2-(2-(Dimethylamino)ethoxy)-4-methoxy-5-(4-(pyrazolo[1,5-a]pyridin-3-yl)benzene)-acrylamide (9). To a solution of Intermediate Q (0.6 g, 1.4 mmol) in 10 mL of THF and 4 mL of water was added 3-chloropropionychloride (0.15 mL, 1.6 mmol) dropwise with stirring. After 22 h of stirring, NaOH (0.7 g, 17 mmol) was added and the mixture was heated at 65° C. for 5 h. After cooling to room temperature, THF was removed under reduced pressure, and the mixture was extracted with $CH_2Cl_2$, dried over $Na_2SO_4$, and concentrated. Chromatography of the crude product (silica gel, $CH_2Cl_2$-MeOH) afforded 0.294 g of Example 9 as a beige solid. $C_{25}H_{27}N_7O_3$ m/z MH+ 474. $^1$H NMR (300 MHz, DMSO) δ 2.28 (s, 6H), 2.61-2.62 (m, 2H), 3.82 (s, 3H), 4.20-4.22 (m, 2H), 5.69-5.73 (m, 1H), 6.20-6.22 (m, 1H), 6.42-6.48 (m, 1H), 6.90-7.11 (m, 2H), 7.15-7.40 (m, 2H), 8.10-8.59 (overlapping m, 4H), 8.72-8.96 (m, 2H), 10.13 (s, 1H) ppm.

Example 10

N-(2-(2-(Dimethylamino)ethoxy)-4-methoxy-5-((4-(1-methyl-1H-indazol-3-yl)pyrimidin-2-yl)amino)phenyl)acrylamide (10)

N-(4-Fluoro-2-methoxy-5-nitrophenyl)-4-(1-methyl-1H-indazol-3-yl)pyrimidin-2-amine (Scheme 8, Intermediate R). Into a 1000-mL 3-necked round-bottom flask purged and maintained with an inert atmosphere of nitrogen, was placed a solution of 1H-indazole (10 g, 84.65 mmol, 1.00 equiv) in N,N-dimethylformamide (500 mL), $I_2$ (21.5 g, 84.65 mmol, 1.00 equiv). This was followed by the addition of KOH (19 g, 338.62 mmol, 4.00 equiv) in several batches at 0° C. The resulting solution was stirred overnight at room temperature. The reaction was then quenched by the addition of 200 mL of aqueous $Na_2S_2O_3$. The resulting solution was extracted with 3×500 mL of ethyl acetate and the organic layers combined. The resulting mixture was washed with 3×500 mL of brine. The mixture was dried over anhydrous sodium sulfate and concentrated under vacuum. The resulting mixture was washed with 1×100 mL of hexane. This resulted in 14 g (68%) of 3-iodo-1H-indazole as a white solid.

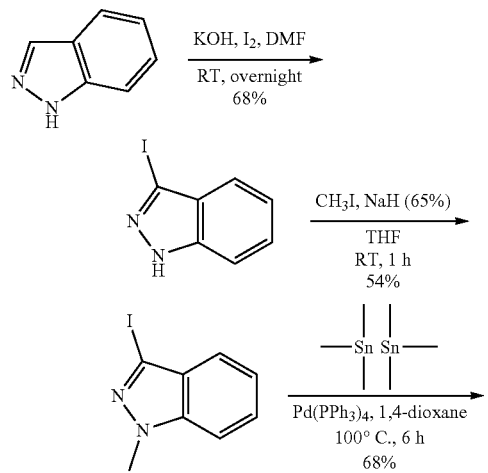

Scheme 8

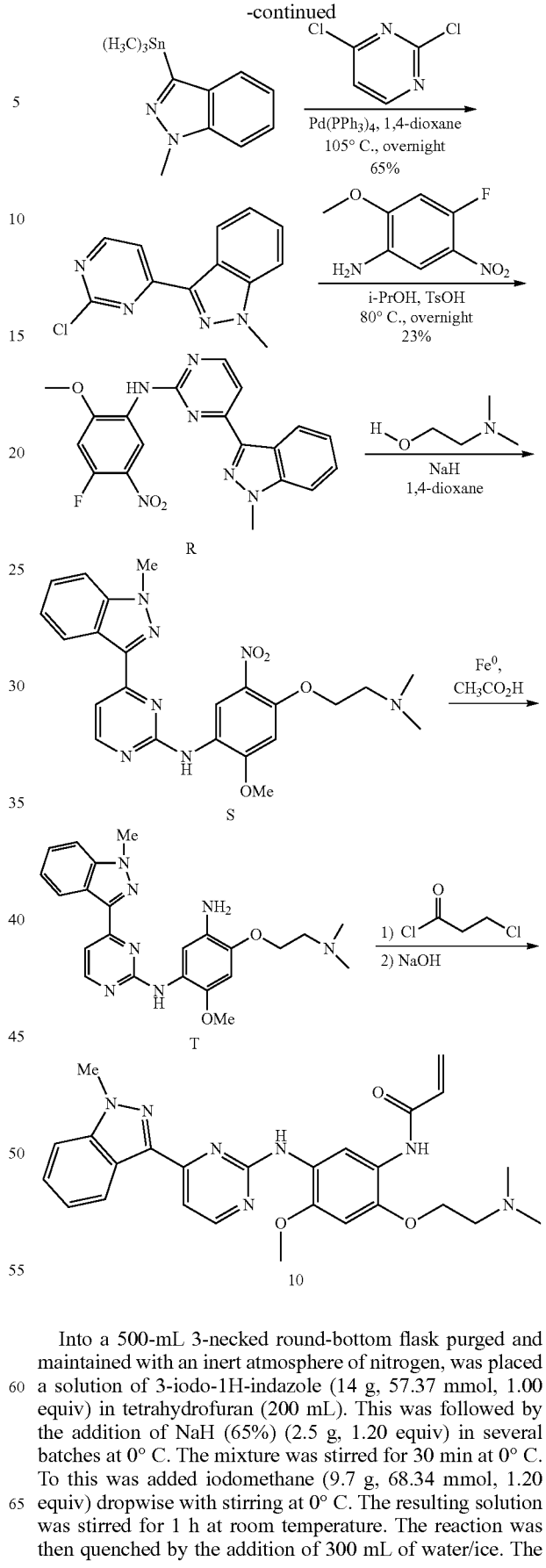

Into a 500-mL 3-necked round-bottom flask purged and maintained with an inert atmosphere of nitrogen, was placed a solution of 3-iodo-1H-indazole (14 g, 57.37 mmol, 1.00 equiv) in tetrahydrofuran (200 mL). This was followed by the addition of NaH (65%) (2.5 g, 1.20 equiv) in several batches at 0° C. The mixture was stirred for 30 min at 0° C. To this was added iodomethane (9.7 g, 68.34 mmol, 1.20 equiv) dropwise with stirring at 0° C. The resulting solution was stirred for 1 h at room temperature. The reaction was then quenched by the addition of 300 mL of water/ice. The resulting solution was extracted with 2×300 mL of ethyl acetate and the organic layers combined. The resulting mixture was washed with 1×300 mL of brine. The mixture was dried over anhydrous sodium sulfate and concentrated under vacuum. The residue was applied onto a silica gel column with ethyl acetate/petroleum ether (1:5). This resulted in 8 g (54%) of 3-iodo-1-methyl-1H-indazole as a yellow solid Into a 500-mL 3-necked round-bottom flask purged and maintained with an inert atmosphere of nitrogen, was placed a solution of 3-iodo-1-methyl-1H-indazole (5 g, 19.38 mmol, 1.00 equiv) in 1,4-dioxane (200 mL), hexamethyldistannane (12 g, 36.63 mmol, 2.00 equiv), tetrakis(triphenylphosphane) palladium (2.2 g, 1.90 mmol, 0.10 equiv). The resulting solution was stirred for 6 h at 100° C. The reaction mixture was cooled to room temperature with a water/ice bath. The reaction was then quenched by the addition of 30 mL of aqueous KF (1 N) dropwise with stirring. The resulting solution was stirred for 0.5 h at room temperature. The resulting solution was diluted with 200 mL of $H_2O$. The resulting solution was extracted with 2×200 mL of ethyl acetate and the organic layers combined. The resulting mixture was washed with 3×200 mL of brine. The mixture was dried over anhydrous sodium sulfate and concentrated under vacuum. The residue was applied onto a silica gel column with ethyl acetate/petroleum ether (1:5). This resulted in 3.9 g (68%) of 1-methyl-3-(trimethylstannyl)-1H-indazole as yellow liquid.

Into a 250-mL 3-necked round-bottom flask purged and maintained with an inert atmosphere of nitrogen, was placed 1-methyl-3-(trimethylstannyl)-1H-indazole (3.9 g, 13.22 mmol, 1.00 equiv), 1,4-dioxane (100 mL), 2,4-dichloropyrimidine (2.0 g, 13.42 mmol, 1.00 equiv), tetrakis(triphenylphosphane) palladium (1.5 g, 1.30 mmol, 0.10 equiv). The resulting solution was stirred overnight at 105° C. The reaction mixture was cooled to room temperature with a water/ice bath. The reaction was then quenched by the addition of 200 mL of water/ice. The solids were collected by filtration. The filter cake was washed with 1×100 mL of $Et_2O$. This resulted in 2.1 g (65%) of 3-(2-chloropyrimidin-4-yl)-1-methyl-1H-indazole as a light yellow solid.

Into a 250-mL 3-necked round-bottom flask, was placed 3-(2-chloropyrimidin-4-yl)-1-methyl-1H-indazole (2.9 g, 11.85 mmol, 1.00 equiv), 4-fluoro-2-methoxy-5-nitroaniline (2.2 g, 11.82 mmol, 1.00 equiv), 2-propanol (80 mL), TsOH (2.4 g, 13.94 mmol, 1.20 equiv). The resulting solution was stirred overnight at 80° C. The reaction mixture was cooled to room temperature with a water/ice bath. The solids were collected by filtration. The filter cake was washed with 100 mL of $CH_3CN$. The solid was dried in an oven. This resulted in 1.06 g (23%) of N-(4-fluoro-2-methoxy-5-nitrophenyl)-4-(1-methyl-1H-indazol-3-yl)pyrimidine-2-amine (Intermediate R) as a yellow solid. (ES, m/z): [M+H]$^+$=395; $^1$H-NMR (300 MHz, DMSO-$d_6$,) δ 8.96 (br, 1H), 8.87-8.85 (d, J=8.4 Hz, 2H), 8.56-8.54 (d, J=5.4 Hz, 1H), 8.49-8.46 (d, J=8.1 Hz, 1H), 7.77-.775 (d, J=8.4 Hz, 1H), 7.58-7.57 (d, J=5.1 Hz, 1H), 7.52-7.47 (t, J=7.2 Hz, 1H), 7.44-7.40 (d, J=13.5 Hz, 1H), 7.26-7.21 (t, J=7.5 Hz, 1H), .4.19 (s, 1H), 4.01 (s, 1H) ppm.

N-(4-(2-(Dimethylamino)ethoxy)-2-methoxy-5-nitrophenyl)-4-(1-methyl-1H-indazol-3-yl)pyrimidine-2-amine (Scheme 8, Intermediate S). To a suspension of NaH (31 mg, 1.3 mmol) in 10 mL of 1,4-dioxane was added 2-dimethylaminoethanol (0.16 mL, 1.3 mmol) dropwise with stirring under $N_2$. After stirring for 1.5 h, Intermediate R (0.2 g, 0.51 mmol) was added portionwise. After 0.5 h, the reaction mixture was quenched with water and extracted with $CH_2Cl_2$. The organic phase was dried over $Na_2SO_4$, filtered and concentrated to yield 0.23 g of N-(4-(2-(dimethylamino)ethoxy)-2-methoxy-5-nitrophenyl)-4-(1-methyl-1H-indazol-3-yl)pyrimidine-2-amine (Intermediate S): m/z MH$^+$=464.

4-(2-(Dimethylamino)ethoxy)-6-methoxy-N$^1$-(4-(1-methyl-1H-indazol-3yl)pyrimidin-2-yl)benzene-1,3-diamine (Scheme 8, Intermediate T). A suspension of N-(4-(2-(dimethylamino)ethoxy)-2-methoxy-5-nitrophenyl)-4-(1-methyl-1H-indazol-3-yl)pyrimidine-2-amine (0.23 g), 0.28 g of Fe$^0$, 10 mL of 70% ethanol/$H_2O$, and 0.5 mL of acetic acid was heated at reflux with stirring for 2 h. The mixture was cooled to room temperature, then filtered. The filtrate was adjusted to pH 10, then extracted with $CH_2Cl_2$. The organic phases were combined, dried over $Na_2SO_4$, filtered and concentrated. The crude product was purified by chromatography (silica gel, $CH_2Cl_2$-1% $NH_4OH$/MeOH gradient) to afford 4-(2-(dimethylamino)ethoxy)-6-methoxy-N$^1$-(4-(1-methyl-1H-indazol-3yl)pyrimidin-2-yl)benzene-1,3-diamine (Intermediate T) as an off-white solid: m/z MH$^+$ 434.

N-(2-(2-(Dimethylamino)ethoxy)-4-methoxy-5-((4-(1-methyl-1H-indazol-3-yl)pyrimidin-2-yl)amino)phenyl) acrylamide (Example 10). To a solution of 4-(2-(dimethylamino)ethoxy)-6-methoxy-N-(4-(1-methyl-1H-indazol-3yl)pyrimidin-2-yl)benzene-1,3-diamine (60 mg, 0.14 mmol) dissolved in 10 mL of 4:1 THF:$H_2O$ was added 3-chloropropionyl chloride (17 mg, 0.14 mmol). After 4 h, NaOH (1.4 mmol, 56 mg) was added and the mixture was heated at reflux for 5 h. THF was removed under reduced pressure, and the aqueous phase was extracted with ethyl acetate. The organic phases were combined, washed with $H_2O$, dried ($Na_2SO_4$) and concentrated. The crude product was purified by chromatography (silica gel, $CH_2Cl_2$-MeOH gradient) to afford Example 10 as a solid: $C_{26}H_{29}N_7O_3$: m/z MH$^+$ 488; $^1$H NMR (300 MHz, DMSO) δ 2.28 (s, 6H), 2.51-2.63 (m, 2H), 3.80 (s, 3H), 4.14-4.44 (overlapping m, 5H), 5.68-5.76 (m 1H), 6.11-6.19 (m, 1H), 6.43-6.48 (m, 1H), 6.95 (s, 1H), 7.11-7.17 (m, 1H), 7.37-7.45 (overlapping m, 2H), 7.68-7.07 (d, 1H, J=8.4 Hz), 8.39-8.43 (overlapping m, 4H), 9.75 (s, 1H) ppm.

Example 11

N-(2-(2-(Dimethylamino)ethoxy)-5-((4-(1-(2-fluoroethyl)-1H-indolyl-3-yl)pyrimidin-2-yl)amino)-4-methoxyphenyl)acrylamide (11)

1-(2-Fluoroethyl)-1H-indole (Scheme 9). Sodium hydride, 60 wt. % in oil (2.3 g, 57.5 mmol) was added to stirred, 0° C., clear, colorless solution of indole (10.1 g, 86.2 mmol) in anhydrous tetrahydrofuran at as rapid a rate consistent with maintaining control of the concomitant hydrogen evolution. Solution was stirred at 0° C. under $N_2$ blanket until gas evolution ceased, and reaction had become a fine white suspension. A solution of 1-fluoro-2-iodoethane (5 g, 29 mmol) in anhydrous tetrahydrofuran (6 mL) was then slowly added via syringe, the ice bath was removed and the pot heated to reflux overnight. The reaction mixture was cooled, diluted with a solution of ammonium chloride (4.6 g, 86 mmol) in DI water (300 mL), transferred to a separatory funnel, and extracted with ethyl acetate. The extract was dried ($CaSO_4$) and evaporated to provide a yellow oil, which was flash chromatographed (silica gel, 100% hexanes) to provide 4.2 g of yellow oil, characterized by LC-MS as a 60/40 mixture of indole to desired product. This impure product was treated with benzene sulfonyl chloride to modify the elution characteristics of the mixture to allow for isolation of the desired product as follows: To a 0° C. solution of the above isolated 60/40 mixture of indole to desired product and tetrabutyl ammonium bisulfate 1.2 g, 3.4 mmol) in anhydrous toluene (100 mL) was added a solution of sodium hydroxide (24.7 g, 617.5 mmol) in DI water (25 mL). To the rapidly stirred, 0° C., mixture was then added benzene sulfonyl chloride (5.5 mL, 43.1 mmol) and the reaction allowed to stir and warm to ambient temperature under $N_2$ blanket overnight.

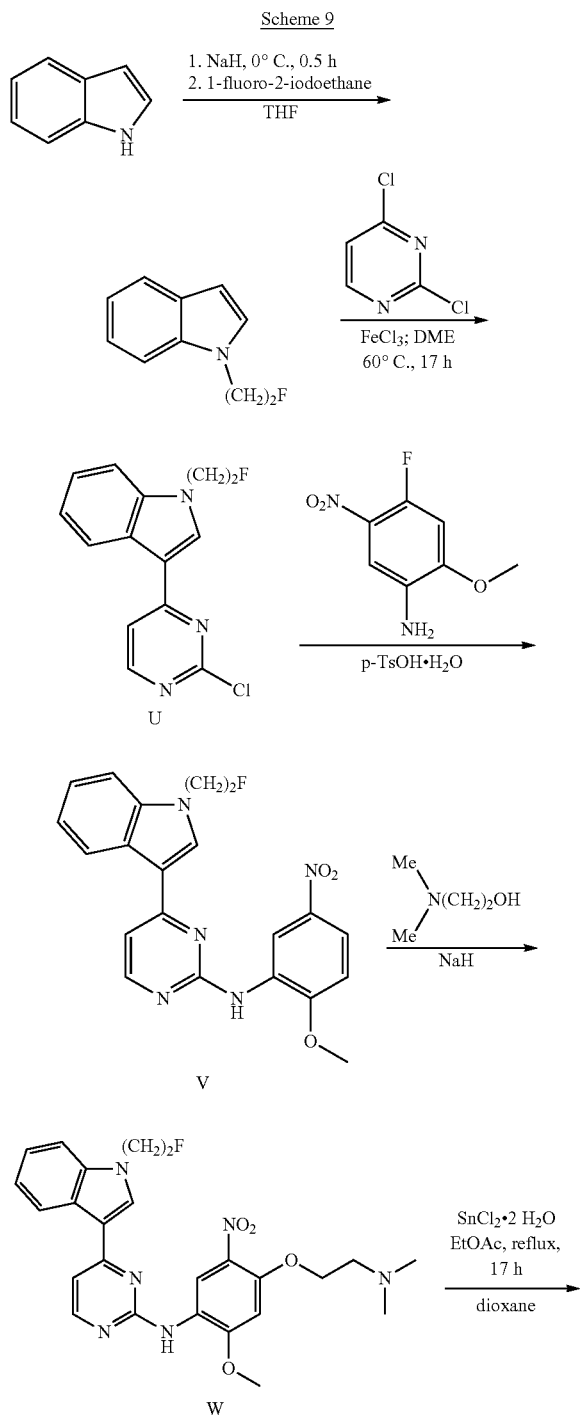

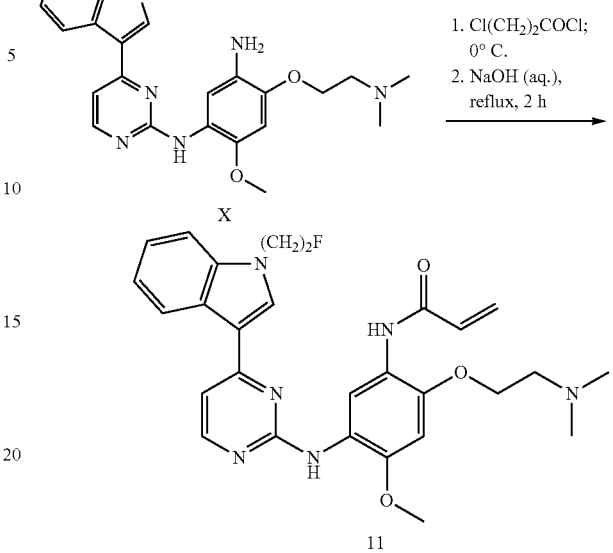

The reaction mixture was then partitioned between ethyl acetate and DI water, the organic phase dried ($CaSO_4$) and flash chromatographed (silica gel, 10% acetone/hexanes) to cleanly resolve the 1-phenylsulfonyl indole from the desired product affording 1.3 g of 1-(2-fluoroethyl)-1H-indole as a clear, colorless liquid. $^1$H NMR (300 MHz, DMSO) δ 4.45 (t, 1H, J=4.9 Hz), 4.54 (t, 1H, J=4.9 Hz), 4.64 (t, 1H, J=4.6 Hz), 4.80 (t, 1H, J=4.4 Hz), 6.46 (dd, 1H, J=3.1, 0.8 Hz), 7.03 (m, 1H), 7.13 (m, 1H), 7.37 (d, 1H, J=3.2 Hz), 7.49 (d, 1H, J=8.3 Hz), 7.55 (m, 1H) ppm. $^{13}$C NMR (75 MHz, DMSO) δ 46.4 (d, $J_{CF}$=19.5 Hz), 83.3 (d, $J_{CF}$=166.5 Hz), 101.4, 110.3, 119.6, 120.9, 121.6, 128.6, 129.3, 136.4 ppm. $C_{10}H_{10}NF$ m/z MH$^+$ 164.

3-(2-Chloropyrimidin-4-yl)-1-(2-fluoroethyl)-1H-indole (Scheme 9, Intermediate U). Ferric chloride (1.3 g, 7.9 mmol) was rapidly added to a stirring, ambient temperature, degassed, clear, colorless solution of 1-(2-fluoroethyl)-1H-indole and 2,4-dichloropyrimidine (1.2 g, 8.3 mmol) dissolved in anhydrous 1,2-dimethoxyethane (80 mL). The resultant black, opaque, solution was stirred at 60° C. for 17 h under dry nitrogen atmosphere, cooled, and partitioned between ethyl acetate and saturated aqueous sodium chloride. The organic phase was dried ($CaSO_4$) and evaporated to provide 2.3 g of purple oil which was purified by flash chromatography (silica gel, 0 to 90% ethyl acetate in hexanes) to yield 557.5 mg of 3-(2-chloropyrimidin-4-yl)-1-(2-fluoroethyl)-1H-indole (U) as a light yellow powder. $^1$H NMR (300 MHz, DMSO) δ 4.60 (t, 1H, J=4.7 Hz), 4.69 (t, 1H, J=4.8 Hz), 4.75 (t, 1H, J=4.4 Hz), 4.90 (t, 1H, J=4.4 Hz), 7.31 (m, 2H), 7.67 (m, 1H), 7.88 (d, 1H, J=5.5 Hz), 8.44 (m, 1H), 8.57 (m, 2H) ppm. $^{13}$C NMR (75 MHz, DMSO) δ 47.2 (d, $J_{CF}$=19.8 Hz), 82.8 (d, $J_{CF}$=167.7 Hz), 111.6, 111.9, 115.0, 122.1, 122.3, 123.4, 125.8, 134.6, 137.8, 159.4, 160.8, 164.9 ppm. $C_{14}H_{11}ClFN_3$ m/z MH$^+$ 276.

N-(4-Fluoro-2-methoxy-5-nitrophenyl)-4-(1-(2-fluoroethyl)-1H-indol-3-yl)pyrimidin-2-amine (Scheme 9, Intermediate V). p-Toluene sulfonic acid monohydrate (442.8 mg, 2.3 mmol) was added to a stirred suspension of 3-(2-chloropyrimidin-4-yl)-1-(2-fluoroethyl)-1H-indole (U) (535.3 mg, 1.9 mmol) and 4-fluoro-2-methoxy-5-nitroaniline (361.4 mg, 1.9 mmol) in 1,4-dioxane (20 mL) and heated to reflux under nitrogen blanket. While approaching reflux temperature the suspended solid dissolved. Reflux was continued overnight, then the reaction was cooled and poured into a rapidly stirred 5% (w/v) solution sodium hydrogen carbonate in DI water (200 mL) to precipitate product. Product was isolated by filtration, washed with water and allowed to dry to yield 921.4 mg of N-(4-fluoro-2-methoxy-5-nitrophenyl)-4-(1-(2-fluoroethyl)-1H-indol-3-yl)pyrimidin-2-amine (V) as a fine yellow powder. $C_{21}H_{17}F_2N_5O_3$ m/z $MH^+$=426.

N-(4-(2-(Dimethylamino)ethoxy)-2-methoxy-5-nitrophenyl)-4-(1-(2-fluoroethyl)-1H-indol-3-yl)pyrimidin-2-amine (Scheme 9, Intermediate W). 2-(Dimethylamino)ethanol (0.8 mL, 7.7 mmol) was slowly added to a stirred, $N_2$ blanketed, ambient temperature, suspension of sodium hydride, 60 wt. % in oil (306.4 mg, 7.7 mmol) in anhydrous 1,4-dioxane (24 mL). Anion formation was allowed to proceed for 0.5 h, then N-(4-fluoro-2-methoxy-5-nitrophenyl)-4-(1-(2-fluoroethyl)-1H-indol-3-yl)pyrimidin-2-amine (intermediate V) (652.0 mg, 1.53 mmol) was added all at once. The reaction immediately turned to a red color, and was allowed to stir. After 10 min., LC-MS reported the reaction to be complete. DI water (5 mL) was added to quench, then the mixture was partitioned between ethyl acetate and saturated aqueous sodium chloride. The organic extract was dried ($CaSO_4$) and evaporated to afford a yellow solid. This solid was recrystallized from boiling ethyl acetate/heptane, which upon cooling, precipitated a bright yellow crystalline powder. The powder was isolated by filtration, washed with heptane, and allowed to dry providing 572.0 mg of N-(4-(2-(dimethylamino)ethoxy)-2-methoxy-5-nitrophenyl)-4-(1-(2-fluoroethyl)-1H-indol-3-yl)pyrimidin-2-amine (W). $^1$H NMR (300 MHz, DMSO) δ 2.27 (s, 6H), 2.71 (t, 2H, J=5.7 Hz), 4.01 (s, 3H), 4.33 (t, 2H, J=5.6 Hz), 4.56 (t, 1H, J=4.6 Hz), 4.65 (t, 1H, J=4.6 Hz), 4.73 (t, 1H, J=4.2 Hz), 4.89 (t, 1H, J=4.6 Hz), 7.01 (s, 1H), 7.10 (m, 1H), 7.25 (m, 2H), 7.61 (d, 1H, J=8.4 Hz), 8.22 (s, 1H), 8.36 (m, 3H), 8.76 (s, 1H) ppm. $^{13}$C NMR (75 MHz, DMSO) δ 46.2, 47.0 (d, $J_{CF}$=19.5 Hz), 57.3, 58.0, 69.0, 82.8 (d, $J_{CF}$=166.6 Hz), 99.2, 108.2, 111.1, 113.4, 119.2, 121.4, 122.4, 122.6, 122.8, 126.0, 131.3, 132.8, 137.6, 150.6, 156.2, 157.7, 160.5, 162.5 ppm. $C_{25}H_{27}FN_6O_4$ m/z $MH^+$=495.

4-(2-(Dimethylamino)ethoxy)-N1-(4-(1-(2-fluoroethyl)-1H-indol-3-yl)pyrimidin-2-yl)-6-methoxybenzene-1,3-diamine (Scheme 9, Intermediate X). Stannous chloride dihydrate (708.3 mg, 3.1 mmol) was added to a stirred, ambient temperature yellow suspension of N-(4-(2-(dimethylamino)ethoxy)-2-methoxy-5-nitrophenyl)-4-(1-(2-fluoroethyl)-1H-indol-3-yl)pyrimidin-2-amine (W) (303.8 mg, 0.6 mmol) in ethyl acetate (30 mL) and heated at reflux under nitrogen blanket for 4 h. The reaction was allowed to cool, then poured into a 5% (w/v) solution of sodium hydrogen carbonate in DI water (200 mL) and stirred for 0.5 h. The multiphase mixture was then filtered through tightly packed celite, with ethyl acetate rinsing of the filter cake. The filtrate was transferred to a separatory funnel and the liquid phases separated. The retained ethyl acetate solution of product was washed with saturated aqueous sodium chloride, dried ($CaSO_4$), and evaporated to provide a red oil which was purified by flash chromatography (silica gel, 2% $NH_4OH$ (aq.) in methanol/ethyl acetate; 0 to 10%) to isolate X as 165.4 mg of red oil. $C_{25}H_{29}FN_6O_2$ m/z $MH^+$=465.

N-(2-(2-(Dimethylamino)ethoxy)-5-((4-(1-(2-fluoroethyl)-1H-indol-3-yl)pyrimidin-2-yl)amino)-4-methoxyphenyl)acrylamide (11, Scheme 9). 3-Chloropropanoyl chloride (38 mL, 0.4 mmol) was slowly added, by syringe, to a rapidly stirred, 0° C., nitrogen blanketed solution of 4-(2-(dimethylamino)ethoxy)-N1-(4-(1-(2-fluoroethyl)-1H-indol-3-yl)pyrimidin-2-yl)-6-methoxybenzene-1,3-diamine (Intermediate X) in anhydrous tetrahydrofuran (20 mL). Upon this addition, precipitate immediately formed. The suspension was stirred at 0° C. for an additional 5 min. then the ice bath was removed. Upon confirmation of complete conversion to the 3-chloropropanamide intermediate, a solution of sodium hydroxide (726.0 mg, 18.2 mmol) in DI water (5.0 mL) was added to the reaction suspension which was heated to reflux for 1 h then cooled and partitioned with brine and additional tetrahydrofuran. The organic extract was dried ($CaSO_4$) and evaporated to yield 445.1 mg of solid orange foam which was purified by gradient flash chromatography (silica gel, 2% $NH_4OH$(aq.) in methanol/ethyl acetate; 0 to 10%), and crystalized from ethyl acetate/heptane to isolate 130 mg of Example 11 as a fine light yellow powder. $^1$H NMR (300 MHz, DMSO) δ 2.28 (s, 6H), 2.58 (t, 2H, J=5.3 Hz), 3.86 (s, 3H), 4.19 (t, 2H, J=5.3 Hz), 4.58 (t, 1H, J=4.6 Hz), 4.67 (t, 1H, J=4.5 Hz), 4.72 (t, 1H, J=4.6 Hz), 4.88 (t, 1H, J=4.6 Hz), 5.75 (dd, 1H, J=10.4, 1.7 Hz), 6.22 (dd, 1H, J=17.0, 1.9 Hz), 6.48 (m, 1H), 6.95 (s, 1H), 7.14 (t, 1H, J=7.4 Hz), 7.22 (m, 2H), 7.60 (d, 1H, J=8.2 Hz), 7.94 (s, 1H), 8.30 (m, 2H), 8.56 (s, 1H), 8.80 (s, 1H), 9.83 (s, 1H) ppm. $^{13}$C NMR (75 MHz, DMSO) δ 45.6, 46.9 (d, $J_{CF}$=19.9 Hz), 56.6, 57.9, 60.2, 69.4, 82.9 (d, $J_{CF}$=168.2 Hz), 101.6, 107.5, 111.1, 113.6, 116.9, 121.4, 122.3, 122.6, 123.2, 126.0, 126.6, 132.6, 133.2, 137.6, 145.3, 147.8, 158.0, 160.7, 162.1, 163.2 ppm. $C_{28}H_{31}FN_6O_3$ m/z $MH^+$=519.

The following non-limiting Examples further illustrate certain aspects of the present invention, which are prepared according to the general Synthetic Schemes 1 to 9 above:

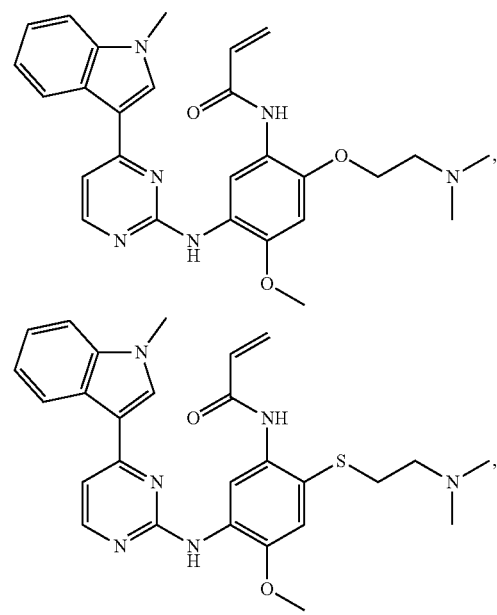

41
-continued
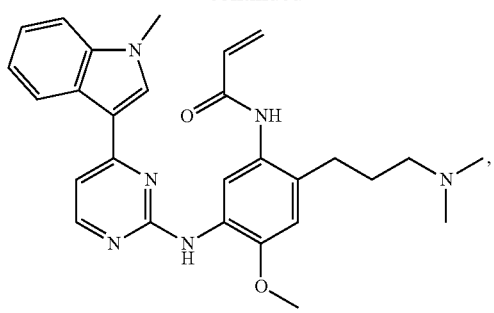
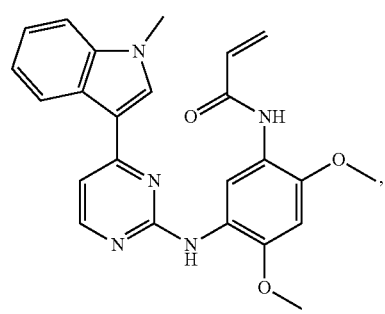
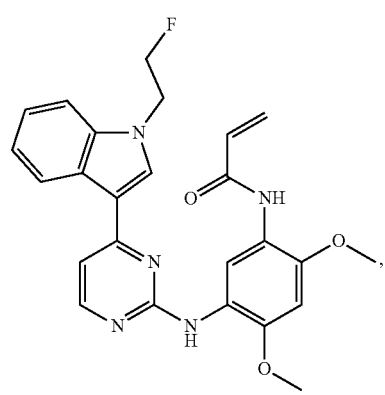
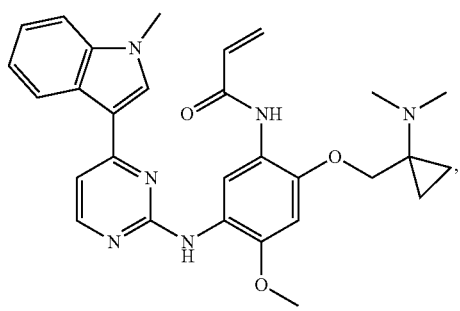
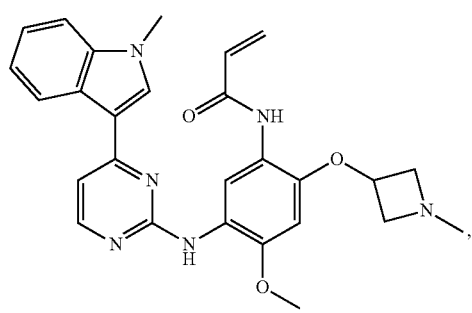
42
-continued
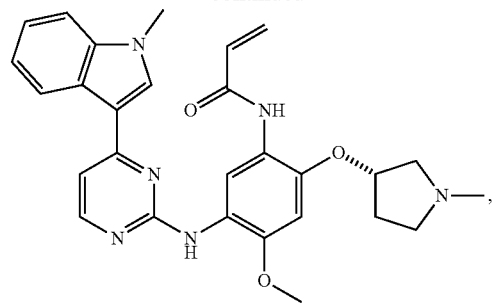
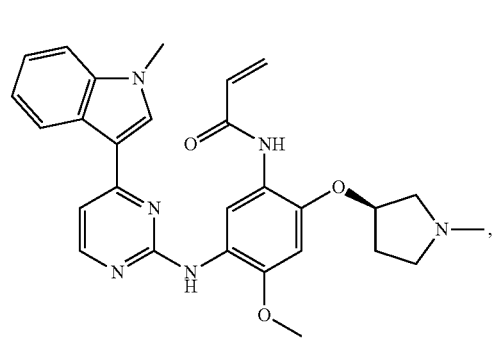
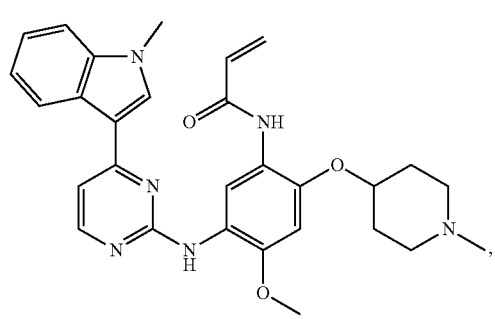
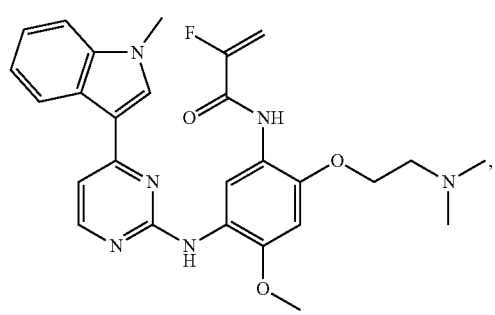
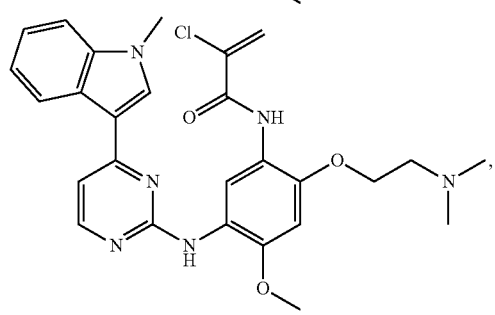

43
-continued
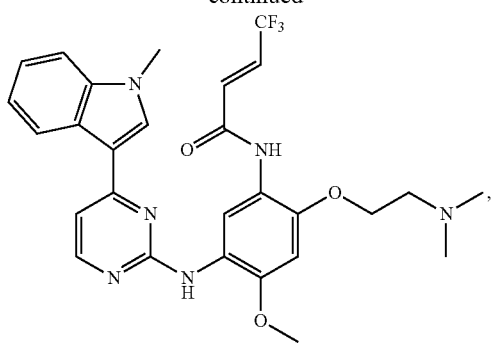
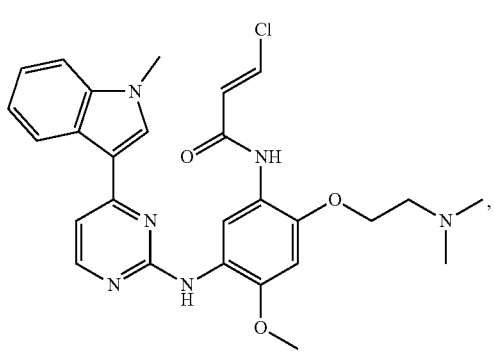
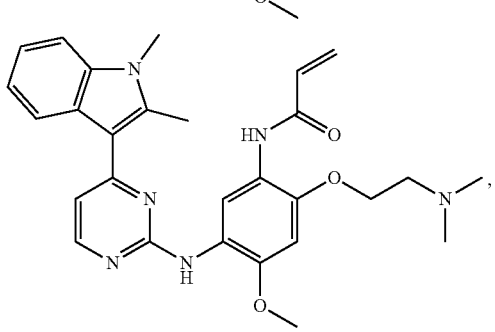
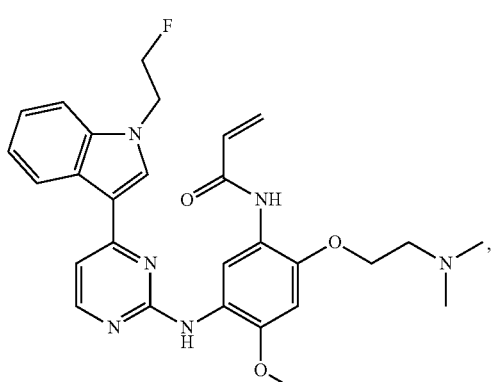
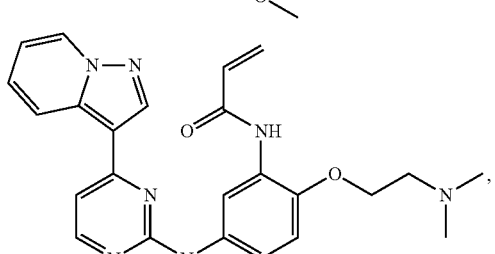
44
-continued
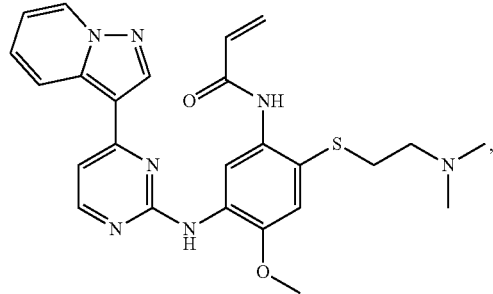
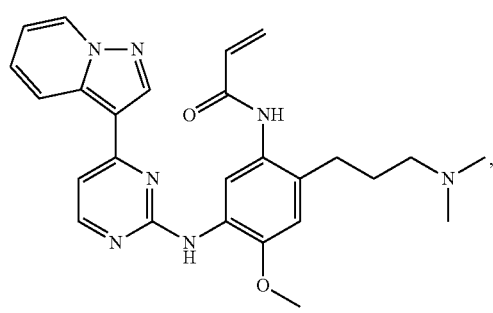
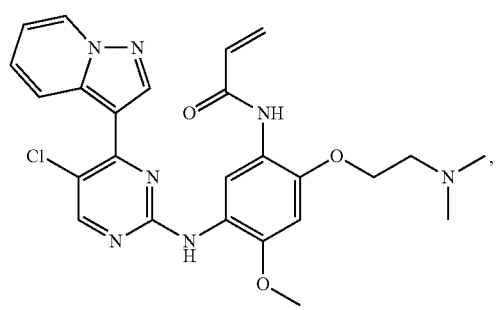
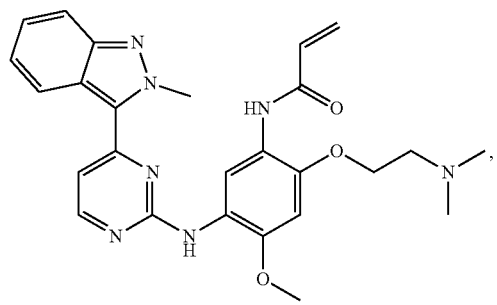
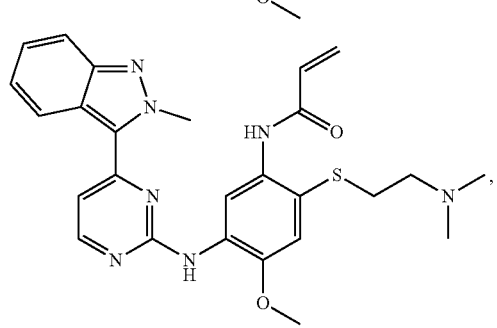

45
-continued
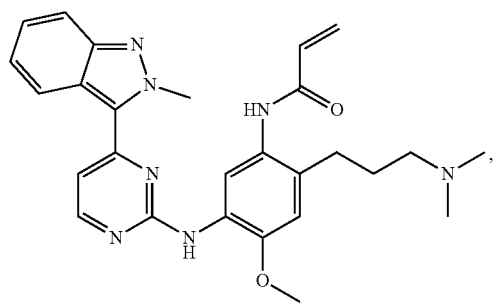
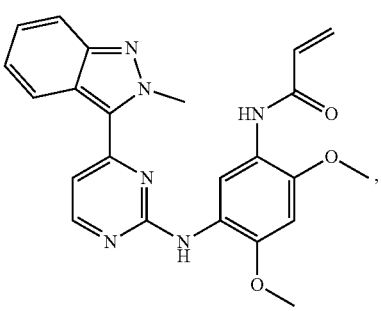
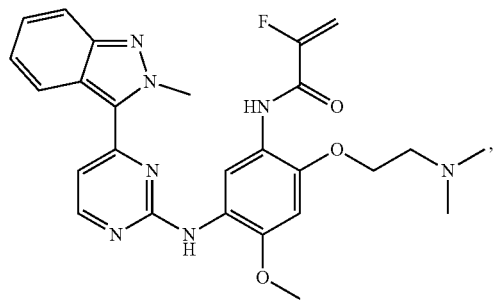
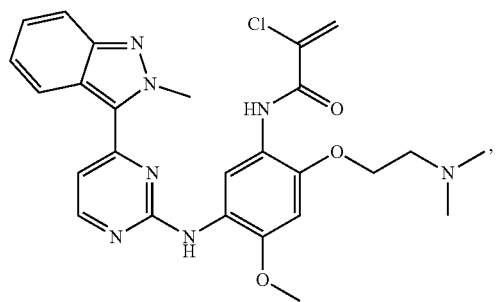
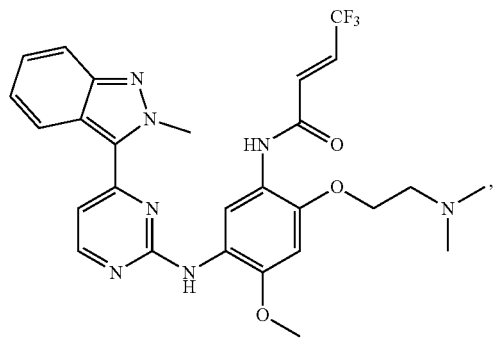
46
-continued
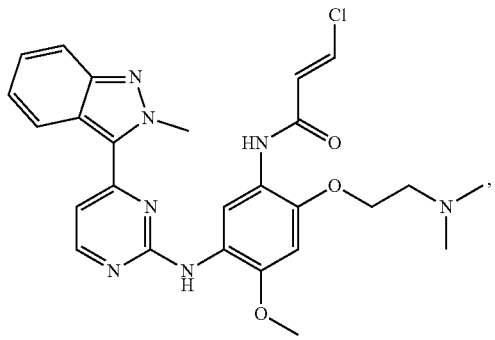
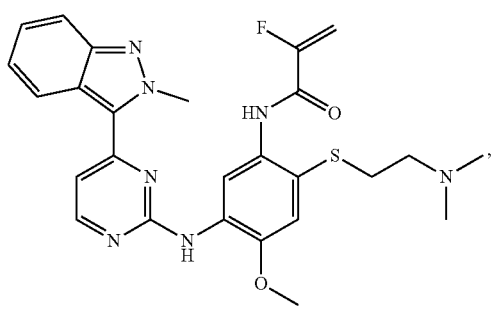
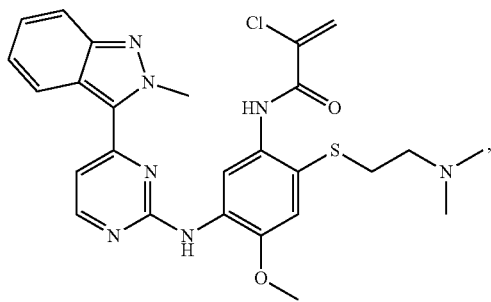
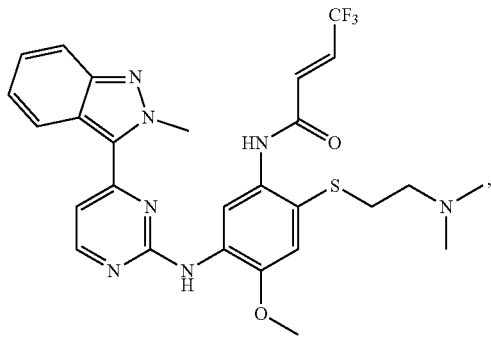
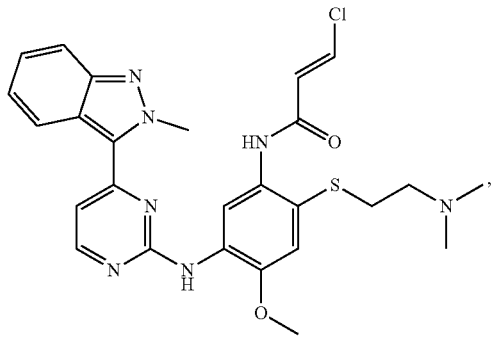

| 47 | 48 |
|---|---|
| -continued | -continued |
| 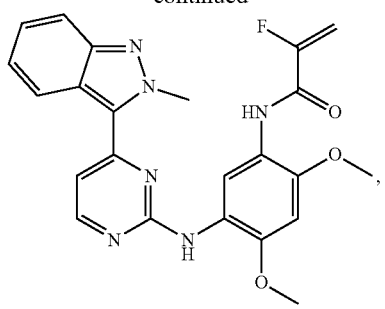 | 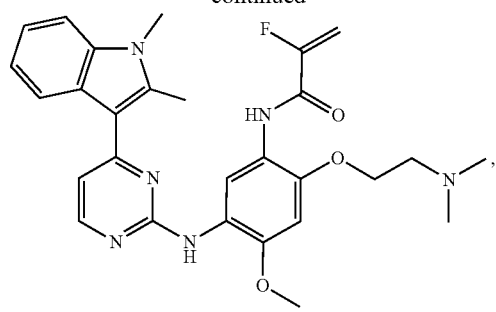 |
| 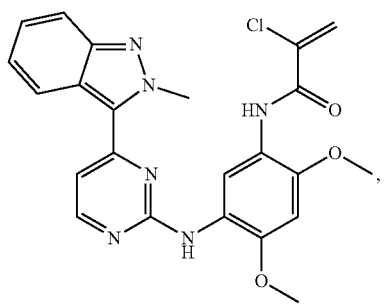 | 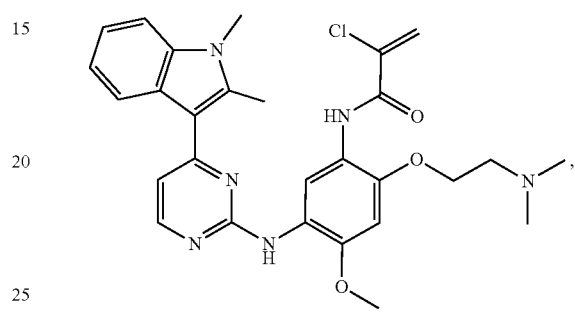 |
| 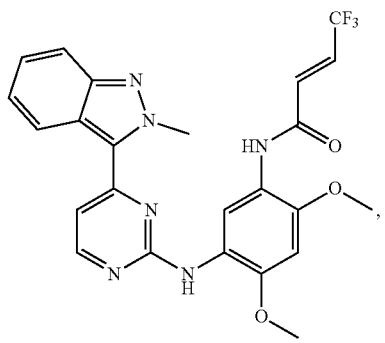 | 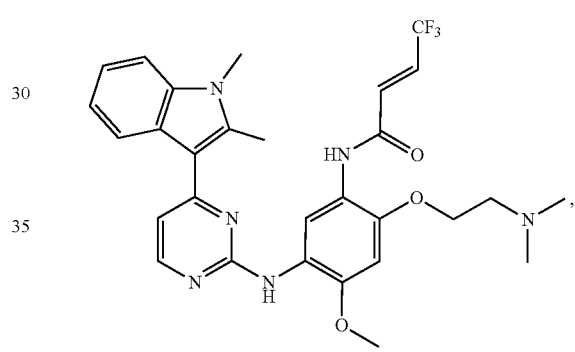 |
| 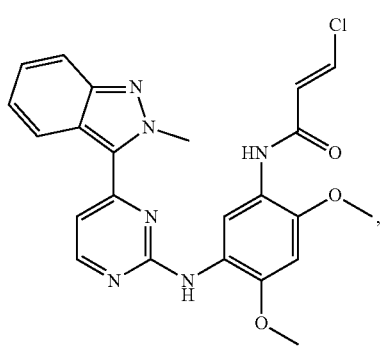 | 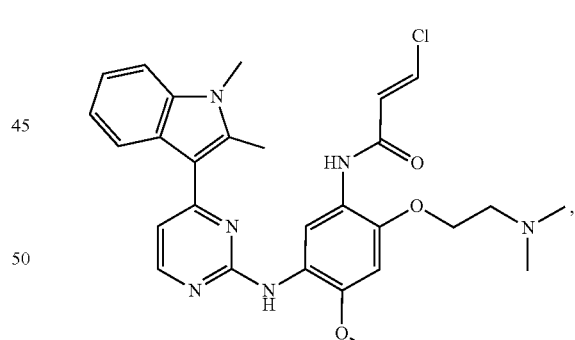 |
| 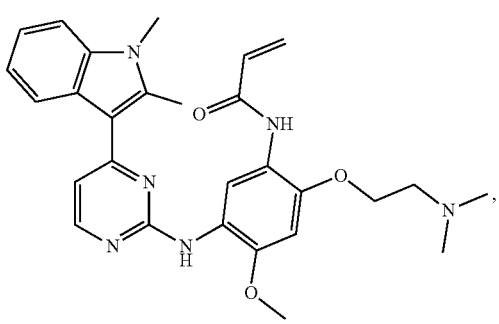 | 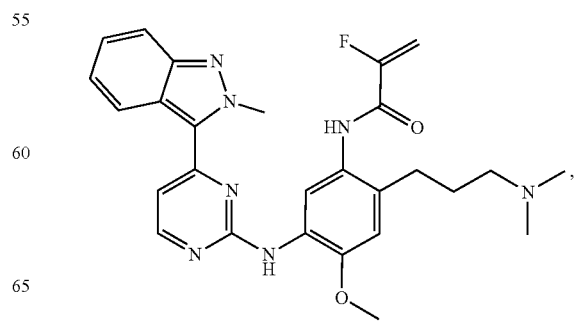 |

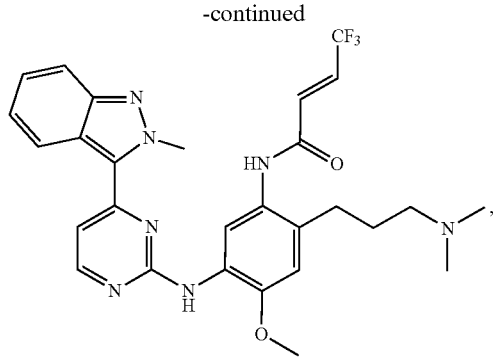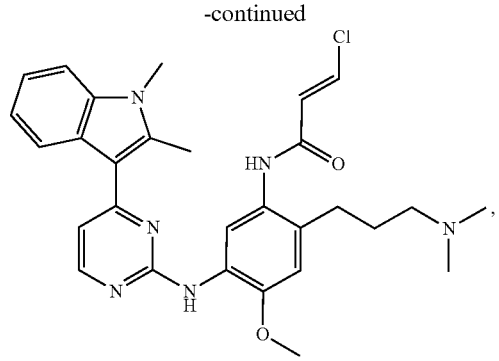

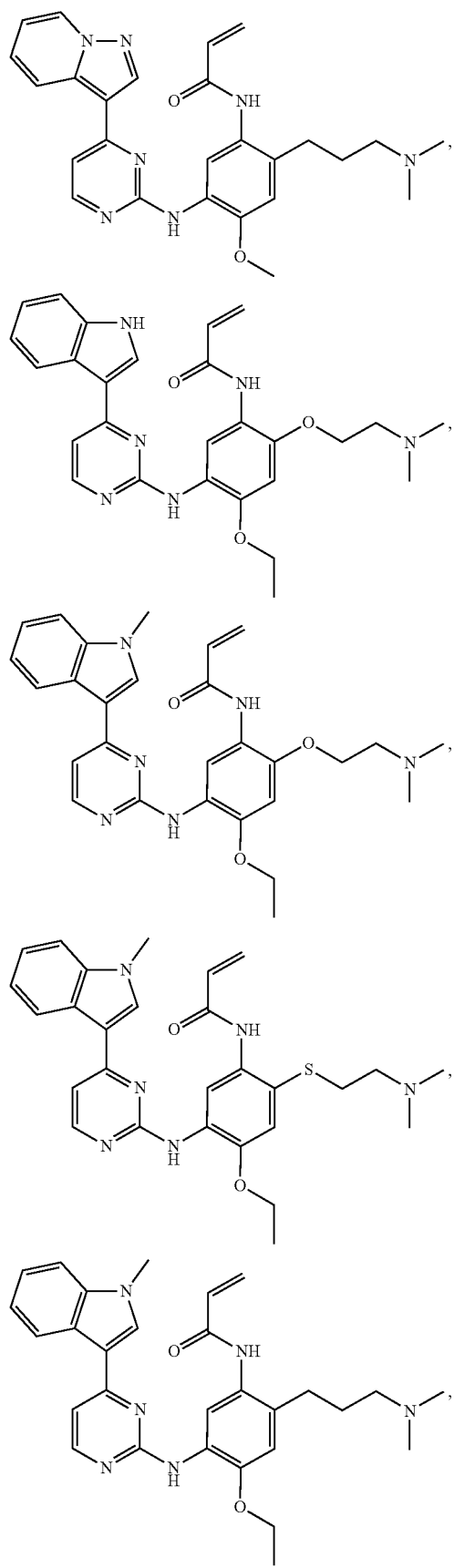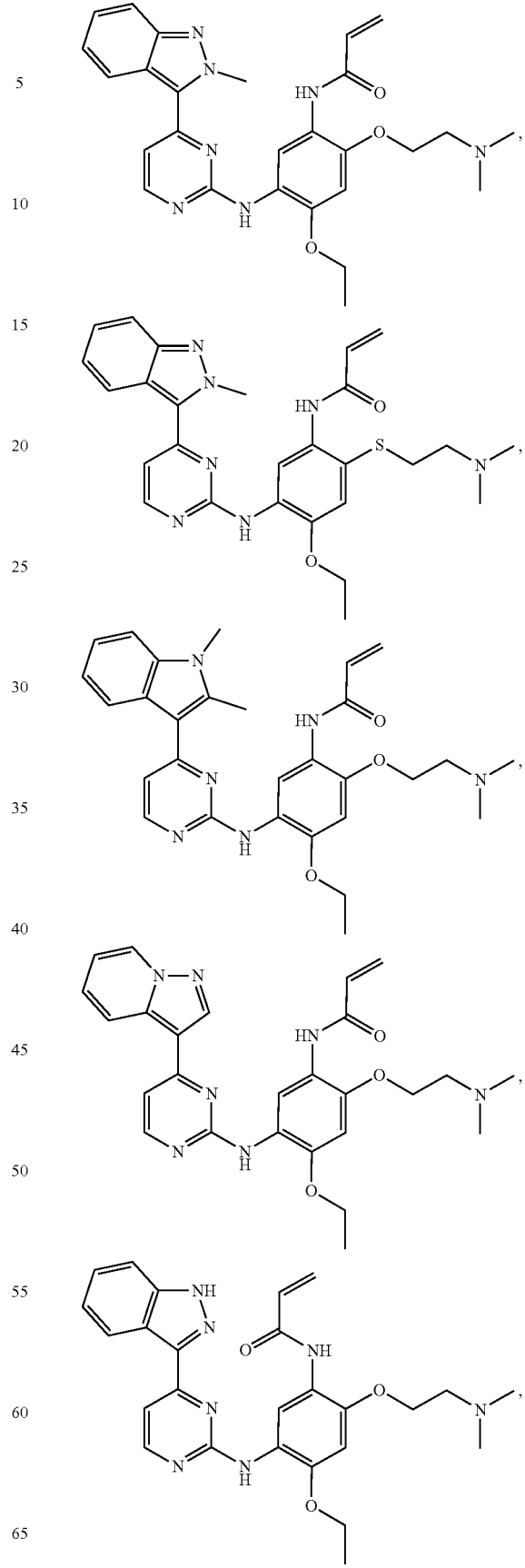

-continued

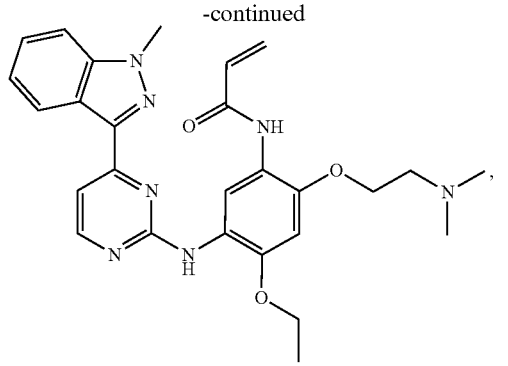

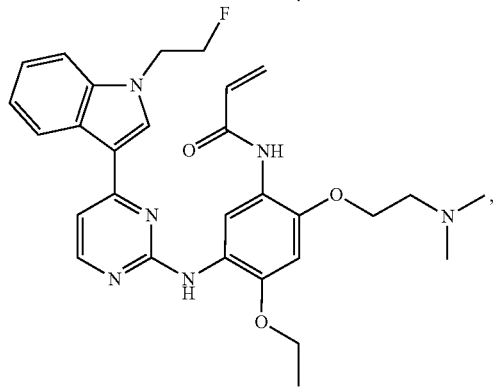

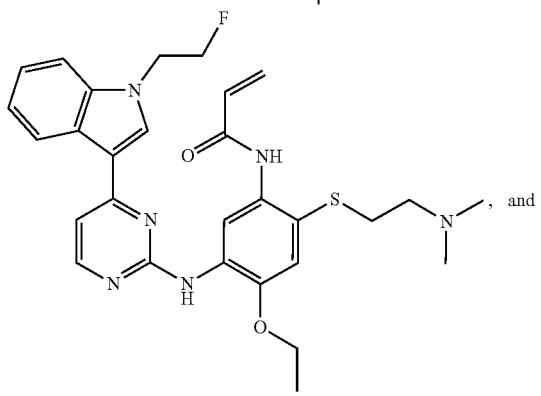, and

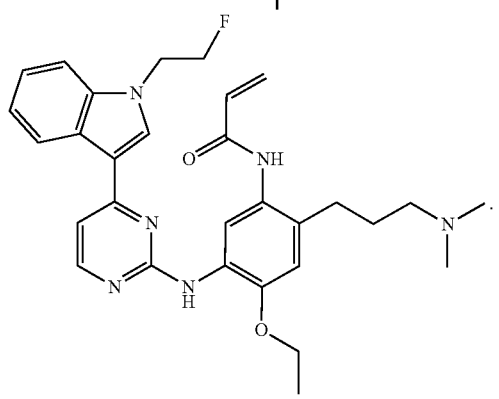.

Biological Assays

Compounds of the formula I as novel EGFR tyrosine kinase inhibitors were evaluated for their activity against EGFR according to the procedures described below.

Cell Culture. A431 (passage 3) and NCI-H1975 (passage 5) cells (ATCC) were started from frozen stocks and cultured in RPMI 1640 medium supplemented with 10% heat-inactivated fetal bovine serum, 1× penicillin/streptomycin/glutamine, 1 mM sodium pyruvate, 10 mM 4-(2-hydroxyethyl)-1-piperazineethanesulfonic acid (HEPES), and 0.25% D-glucose (growth medium) in T175 flasks in a humidified 30° C., 5% $CO_2$ incubator. The cell monolayer was dispersed by 5 minute exposure to 0.25% Trypsin/EDTA solution (Life Technologies) and the solution was neutralized with a fresh growth medium. Pooled cells were pelleted by centrifugation (200× g, 8 min.), resuspended in the growth medium, and an aliquot was removed for cell counting using an automated cell counter (Logos Biosystems). The cells maintained normal morphology and growth characteristics during the period of the study.

Cell Proliferation Assay. Dispersed cells were pooled by centrifugation (200×g, 8 min.) and resuspended in a fresh medium to a concentration of 1.00 E+04 cells/ml. 200 μL of the cell suspension was added to each well (2,000 cells/well) of a black-walled 96 well plate and the cells were allowed to attach overnight under normal culture conditions. After overnight culturing, 1 μL of a test compound (n=3 per concentration) was added per well to achieve final concentrations of 10, 3.33, 1.11, 0.370, 0.124, 0.0412, 0.0137, 0.0046, and 0.0015 μM. The final DMSO concentration in the well was 0.5% v/v. Vehicle, non-treated, and cell-free wells were also included in the assay. The cells were cultured under normal conditions for 72 hours with daily visual inspection.

Cell proliferation was measured using the dye Alamar Blue (resazurin). Resazurin is reduced by cellular enzymes to resorufin, which is fluorescent (544 nM excitation, 612 nm emission). Fluorescence intensity was proportional to cell number. A resazurin stock solution was prepared in a phosphate-buffered saline (PBS) to a stock concentration of 440 μM. The resazurin stock solution (40 μL each) was added to each well at hour 67 of the 72 hour incubation period. The plate was returned to normal culture conditions and fluorescence measurements were collected using a Cytation 3 multimode plate reader (Biotek) at 72 hours.

Data Analysis. Fluorescence measurements were normalized against cell-free (background) readings and the total growth over 72 hour time period was determined versus the average of the vehicle control wells. Average and standard deviation values were determined for each condition (n=3).

Table 1 contains illustrative data from study of representative compounds of the present invention, which demonstrate their excellent selectivity for inhibition of the growth of H1975 (double mutant) cells over A431 (wild type) cells.

TABLE 1

Biological activity of selected compounds in the A431 (wild type) and H1975 (double mutant) cell proliferation assays.

| Example | A431 $IC_{50}$ (μM)[a] | H1975 $IC_{50}$ (μM)[a] |
| --- | --- | --- |
| 1 | + | +++ |
| 2 | + | +++ |
| 3 | + | ++ |
| 4 | + | +++ |
| 5 | ++ | ++ |
| 8 | ++ | +++ |
| 9 | + | +++ |
| 10 | ++ | +++ |
| 11 | ++ | +++ |

[a] An $IC_{50}$ value greater than 1.0 μM is represented by "+"; an $IC_{50}$ in the range of 0.1-1.0 μM is represented by "++", and an $IC_{50}$ value below 0.1 μM is represented by "+++".

The in vivo anticancer activity of Examples 1 and 2 is also illustrated in FIGS. 1-4.

Antitumor Activity of Example 1 in the H1975 Mouse Xenograft Model. The in vivo anticancer activity of Example 1 against tumors with the L858R/T790M double mutation is illustrated in FIG. 1. Example 1 was evaluated in subcutaneously-implanted H1975 human non-small cell lung carcinoma xenographs in female nude mice at 6.25, 12.5 and 25 mg/kg. Example 1 was dosed orally once a day for 14 days (days 6-19). At all doses, Example 1 was well tolerated, resulting in no treatment-related mortality. Treatment with 1 at 6.25, 12.5 and 25 mg/kg produced a median time to evaluation size of 28.9, 31.6 and 34.3 days, respectively, resulting in a statistically significant (P<0.05) tumor growth delay of 14, 16.7 and 19.3 days, respectively. At 25 mg/kg, treatment produced a 100% incidence of complete regressions and 10% of the mice were tumor free survivors.

Figure 2:
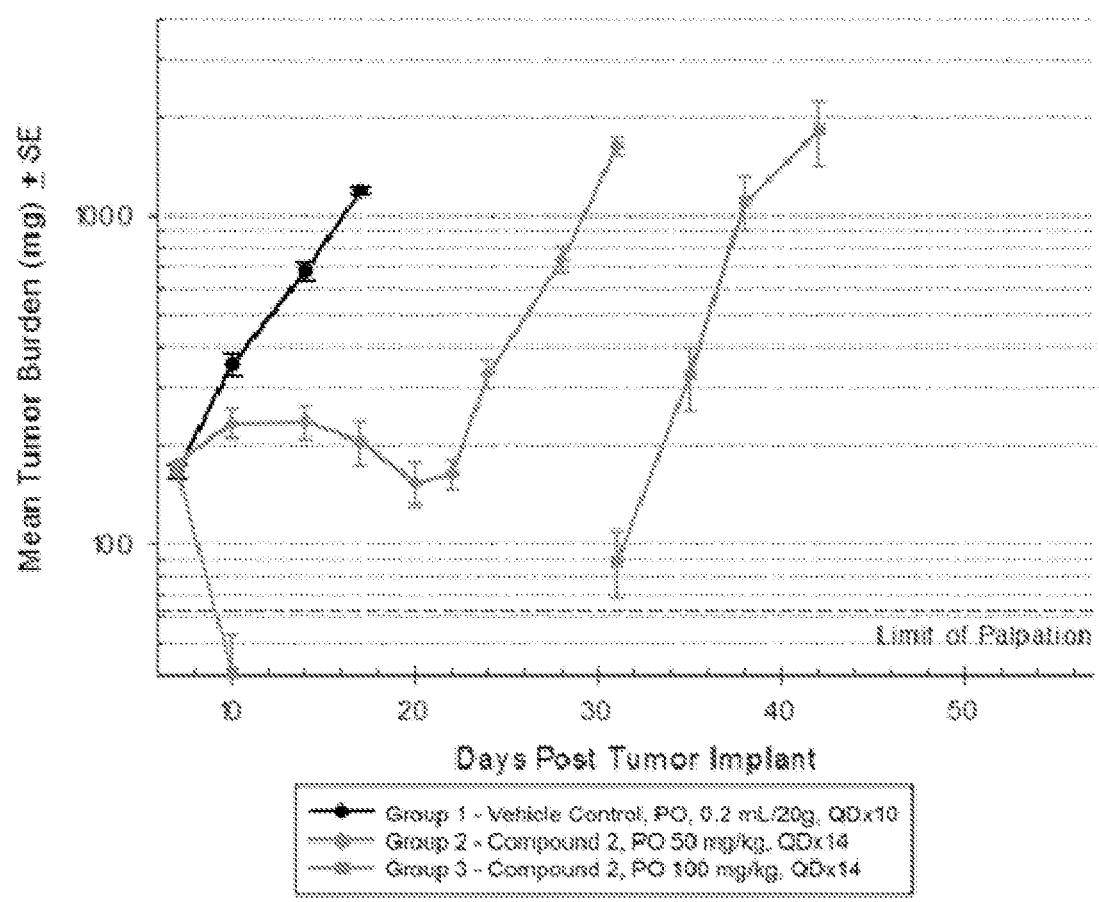
FIG. 2 illustrates the H1975 tumor growth inhibition assay results for Example 2 in mice.

Antitumor Activity of Example 2 in the H1975 Mouse Xenograft Model. The in vivo anticancer activity of Example 2 against tumors with the L858R/T790M double mutation is illustrated in FIG. 2. Example 2 was evaluated in subcutaneously-implanted H1975 human non-small cell lung carcinoma xenographs in female nude mice at 50 and 100 mg/kg. Example 2 was dosed orally once a day for 14 days (days 7-20). At 100 mg/kg oral dosing, Example 2 was well tolerated and produced significant (P<0.05) anticancer activity based upon the % tumor growth inhibition values (% TGI) of 110.5%, 116.6% and 116.6%, which were calculated from the median tumor burdens on days 10, 14 and 17, respectively. Time to evaluation size (750 mm$^3$) was 39.6 days, resulting in a tumor growth delay (T-C) of 22.2 days, which is also statistically significant. Treatment produced a 100% incidence of complete tumor regression and 12.5% of the mice remained tumor free (TFS) at the completion of the study.

Figure 3:
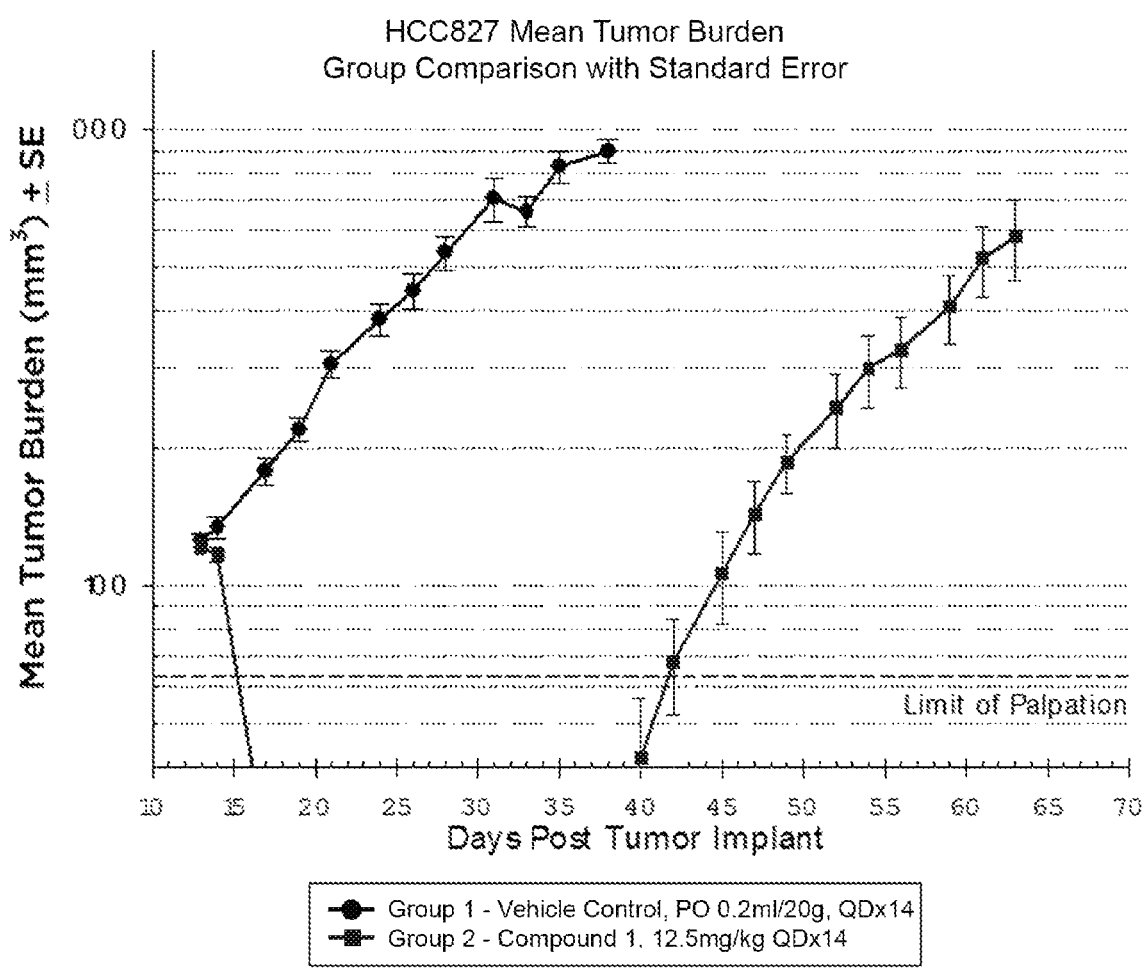
FIG. 3 illustrates the HCC827 tumor growth inhibition assay results for Example 1 in mice.
Figure 4:
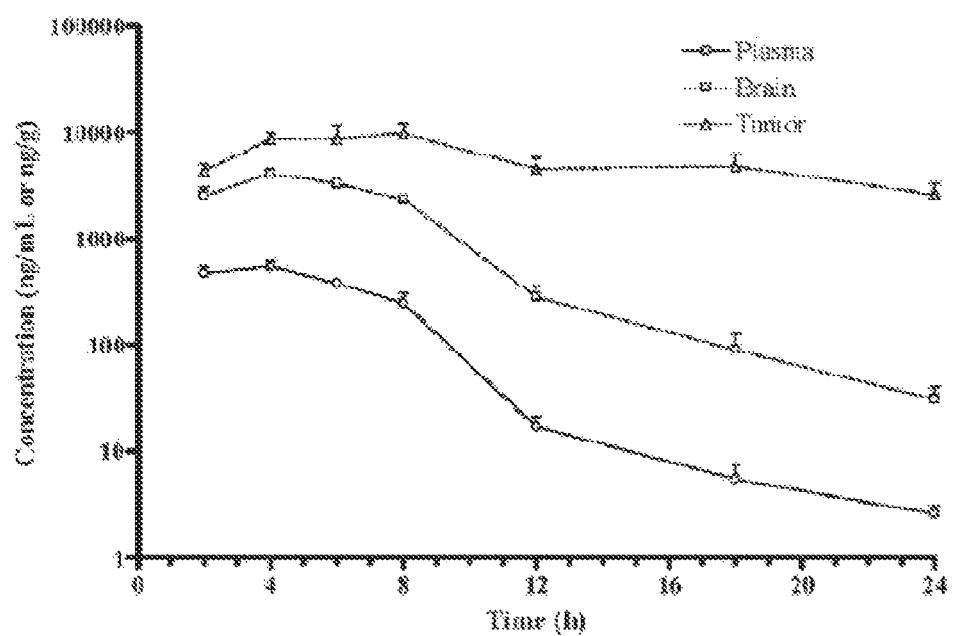
FIG. 4 illustrates the average concentrations of Example 1 in plasma, brain and tumor tissues in mice following oral administration of a 25 mg/kg dose in the HCC827 mouse xenograft model.

Antitumor Activity of Example 1 in the HCC827 Mouse Xenograft Model. The in vivo anticancer activity of Example 1 against tumors with the delE746-A750 activating mutation is illustrated in FIG. 3. Example 1 was evaluated in a subcutaneously-implanted HCC827 human non-small cell lung carcinoma xenographs in female nude mice at 6.25 mg/kg. Example 1 was dosed orally once a day for 14 days (days 13-26). At 6.25 mg/kg oral dosing, 1 was well tolerated, resulting in no treatment-related mortality. Treatment with 1 produced a median time to evaluation size of 61.5 days, resulting in a statistically significant (P<0.05) tumor growth delay of 33.2 days. Treatment produced a 100% incidence of complete tumor regression at the completion of dosing. FIG. 4 shows the average concentration of Example 1 in plasma, brain and tumor tissues following a 25 mg/kg oral dose in this model.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims.

What is claimed is:

1. A method of treating a disease or disorder associated with mutant EGFR activity, comprising administering to a patient in need of treatment a therapeutically effective amount of a compound of formula 1, or a pharmaceutically acceptable salt thereof

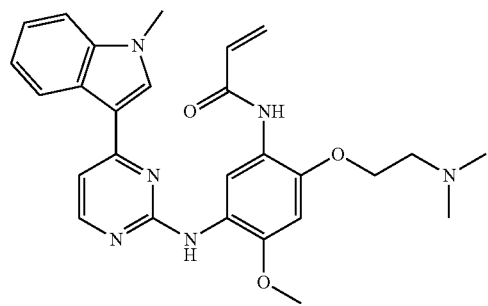

wherein the disease or disorder is associated with a delE746-A750 activating mutant of EGFR.

2. The method of claim 1, wherein the disease or disorder is a cancer selected from the group consisting of brain cancer, lung cancer, kidney cancer, bone cancer, liver cancer, bladder cancer, head and neck cancer, esophageal cancer, stomach cancer, colon cancer, rectum cancer, breast cancer, ovarian cancer, melanoma, skin cancer, adrenal cancer, cervical cancer, lymphoma, and thyroid tumors and their complications.

3. The method of claim 2, wherein the cancer is brain cancer or lung cancer.

4. The method of claim 1, in combination with administering to the patient a second therapeutic agent.

5. The method of claim 4, wherein the second therapeutic agent is a chemotherapeutic agent.

6. The method of claim 4, wherein the second therapeutic agent is a different EGFR modulator.

7. A method of preparing a compound of formula (I), comprising reacting an intermediate compound C with 3-chloropropionyl chloride in the presence of a base to form the compound of formula (I):

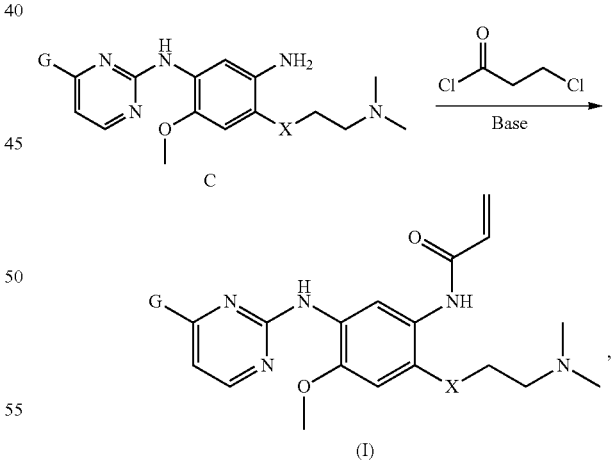

wherein G is 1-methyl-1H-indol-3-yl, 1-(2-fluoroethyl)-1H-indol-3-yl, 1,2-dimethyl-1H-indol-3-yl, pyrazolo[1,5-a]-pyridin-3-yl, or 1-methyl-1H-indazol-3-yl; and X is O, S, or $CH_2$ wherein:
when X is O or S, further comprising converting compound A to intermediate compound B through displacement of the fluoro (F) group in the compound A by $HX(CH_2)_2N(CH_3)_2$ in the presence of a base and converting the intermediate compound B to the intermediate compound C by reduction of the nitro group on the compound B:

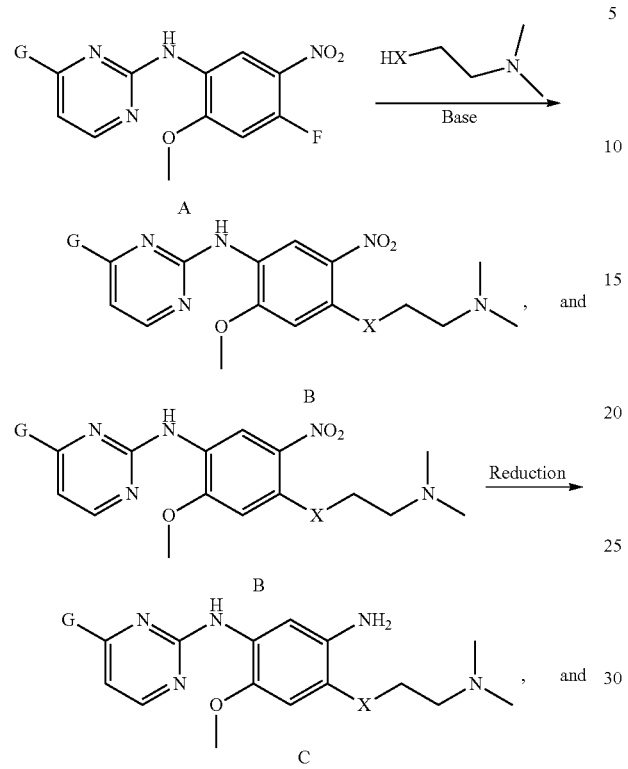

when X is CH₂, further comprising converting compound A to intermediate compound D by displacement of the fluoro (F) group in the compound A with 3-dimethyl- amino-1-propynyl lithium and converting the compound D to the compound C through hydrogenation of the compound D in the presence of a palladium or platinum catalyst:

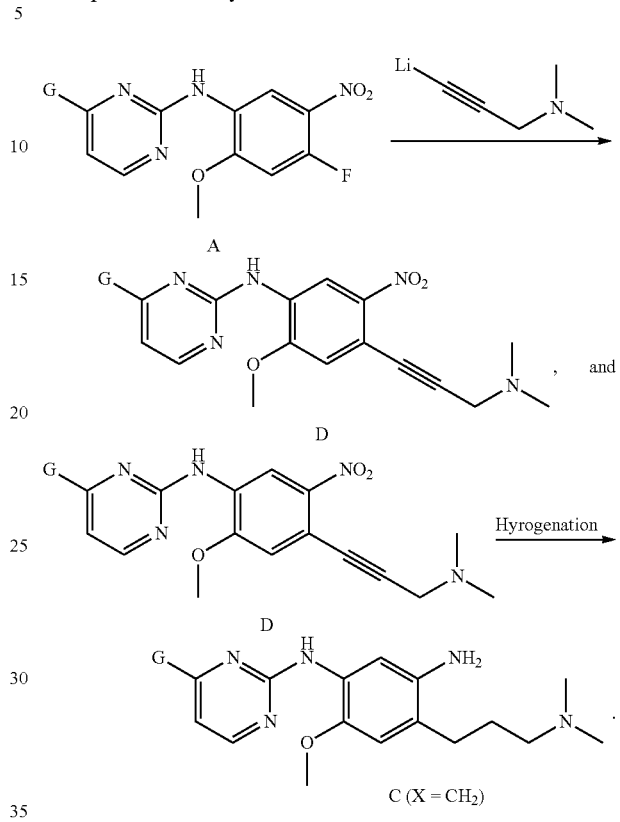

* * * * *